(12) United States Patent
Martin

(10) Patent No.: US 10,610,678 B2
(45) Date of Patent: Apr. 7, 2020

(54) BI-DIRECTIONAL, PRESSURE-ACTUATED MEDICAL VALVE WITH IMPROVED FLUID FLOW CONTROL AND METHOD OF USING SUCH

(71) Applicant: AngioDynamics, Inc., Latham, NY (US)

(72) Inventor: Fredrick L. Martin, Ballston Lake, NY (US)

(73) Assignee: AngioDynamics, Inc., Latham, NY (US)

( * ) Notice: Subject to any disclaimer, the term of this patent is extended or adjusted under 35 U.S.C. 154(b) by 161 days.

(21) Appl. No.: 15/674,626

(22) Filed: Aug. 11, 2017

(65) Prior Publication Data

US 2018/0043149 A1 Feb. 15, 2018

Related U.S. Application Data

(60) Provisional application No. 62/373,400, filed on Aug. 11, 2016.

(51) Int. Cl.
*A61M 39/24* (2006.01)
*F16K 15/14* (2006.01)

(52) U.S. Cl.
CPC ........... *A61M 39/24* (2013.01); *F16K 15/147* (2013.01); *A61M 2039/242* (2013.01); *A61M 2039/246* (2013.01); *A61M 2039/2426* (2013.01)

(58) Field of Classification Search
CPC ............ A61M 39/24; A61M 2039/242; A61M 2039/2426; A61M 2039/246; A61M 2039/2493; F16K 15/147; F16K 31/126; F16K 7/17
See application file for complete search history.

(56) References Cited

U.S. PATENT DOCUMENTS

| 2,446,571 A | 8/1948 | Browne |
| 3,113,586 A | 12/1963 | Edmark |
| 3,159,175 A | 12/1964 | Macmillan |
| 3,159,176 A | 12/1964 | Gifford et al. |

(Continued)

FOREIGN PATENT DOCUMENTS

| CN | 102155808 | 8/2011 |
| DE | 3048203 | 7/1982 |

(Continued)

OTHER PUBLICATIONS

Hoffer et al., Prospective Randomized Comparison of Valved Versus Nonvalved Peripherally Inserted Central Vein Catheters, pp. 1393-1398, Nov. 1999.

(Continued)

*Primary Examiner* — Emily L Schmidt
*Assistant Examiner* — Tiffany Legette
(74) *Attorney, Agent, or Firm* — Peter J. Flora, Esq.

(57) ABSTRACT

A bi-directional, pressure-actuated medical valve assembly for improved control of fluids and related methods of use are described. The pressure-actuated, bi-directional valve includes a first flow control portion permitting fluid to flow in a first direction when subjected to a first pressure threshold and a second control flow portion for permitting fluid to flow in a second direction when subjected to a second pressure threshold. Other embodiments are described and claimed.

20 Claims, 11 Drawing Sheets

(56) References Cited

U.S. PATENT DOCUMENTS

| | | |
|---|---|---|
| 3,477,438 A | 11/1969 | Allen et al. |
| 3,514,438 A | 5/1970 | Bixler et al. |
| 3,525,357 A | 8/1970 | Koreski |
| 3,621,557 A | 11/1971 | Cushman et al. |
| 3,669,323 A | 6/1972 | Kenneth et al. |
| 3,673,612 A | 7/1972 | Edward et al. |
| 3,674,183 A | 7/1972 | Venable et al. |
| 3,710,942 A | 1/1973 | Rosenberg |
| 3,788,327 A | 1/1974 | Donowitz et al. |
| 3,811,466 A | 5/1974 | Ohringer |
| 3,848,579 A | 11/1974 | Villa-Real |
| 3,941,149 A | 3/1976 | Mittleman |
| 3,955,594 A | 5/1976 | Snow |
| 4,072,146 A | 2/1978 | Howes |
| 4,142,525 A | 3/1979 | Binard et al. |
| 4,143,853 A | 3/1979 | Abramson |
| 4,244,379 A | 1/1981 | Smith |
| 4,387,879 A | 6/1983 | Tauschinski |
| 4,405,316 A | 9/1983 | Mittleman |
| 4,434,810 A | 3/1984 | Atkinson |
| 4,447,237 A | 5/1984 | Frisch et al. |
| 4,468,224 A | 8/1984 | Enzmann et al. |
| 4,502,502 A | 3/1985 | Krug |
| 4,524,805 A | 6/1985 | Hoffman |
| 4,543,087 A | 9/1985 | Sommercorn et al. |
| 4,552,553 A | 11/1985 | Schulte et al. |
| 4,610,665 A | 9/1986 | Matsumoto et al. |
| 4,616,768 A | 10/1986 | Flier |
| 4,646,945 A | 3/1987 | Steiner et al. |
| 4,673,393 A | 6/1987 | Suzuki et al. |
| 4,681,572 A | 7/1987 | Tokarz et al. |
| 4,692,146 A | 9/1987 | Hilger |
| 4,722,725 A | 2/1988 | Sawyer et al. |
| 4,790,832 A | 12/1988 | Lopez |
| 4,798,594 A | 1/1989 | Hillstead |
| 4,801,297 A | 1/1989 | Mueller |
| 4,908,028 A | 3/1990 | Colon et al. |
| 4,944,726 A | 7/1990 | Hilal et al. |
| 4,946,448 A | 8/1990 | Richmond |
| 4,960,412 A | 10/1990 | Fink |
| 4,991,745 A | 2/1991 | Brown |
| 5,000,745 A | 3/1991 | Guest et al. |
| 5,009,391 A | 4/1991 | Steigerwald |
| 5,030,210 A | 7/1991 | Alchas |
| 5,084,015 A | 1/1992 | Moriuchi |
| 5,098,405 A | 3/1992 | Peterson et al. |
| 5,125,893 A | 6/1992 | Dryden |
| 5,143,853 A | 9/1992 | Walt |
| 5,147,332 A | 9/1992 | Moorehead |
| 5,149,327 A | 9/1992 | Oshiyama |
| 5,167,638 A | 12/1992 | Felix et al. |
| 5,169,393 A | 12/1992 | Moorehead et al. |
| 5,176,652 A | 1/1993 | Littrell |
| 5,176,662 A | 1/1993 | Bartholomew et al. |
| 5,201,722 A | 4/1993 | Moorehead et al. |
| 5,205,834 A | 4/1993 | Moorehead et al. |
| 5,249,598 A | 10/1993 | Schmidt |
| 5,253,765 A | 10/1993 | Moorehead et al. |
| 5,254,086 A | 10/1993 | Palmer et al. |
| 5,255,676 A | 10/1993 | Russo |
| 5,324,274 A | 6/1994 | Martin |
| 5,330,424 A | 7/1994 | Palmer et al. |
| 5,336,203 A | 8/1994 | Goldhardt et al. |
| 5,360,407 A | 11/1994 | Leonard et al. |
| 5,370,624 A | 12/1994 | Edwards et al. |
| 5,395,352 A | 3/1995 | Penny |
| 5,396,925 A | 3/1995 | Poli |
| 5,399,168 A | 3/1995 | Wadsworth, Jr. et al. |
| 5,401,255 A | 3/1995 | Sutherland et al. |
| D357,735 S | 4/1995 | McPhee |
| 5,405,340 A | 4/1995 | Fageol et al. |
| 5,411,491 A | 5/1995 | Goldhardt et al. |
| 5,453,097 A | 9/1995 | Paradis |
| 5,454,784 A | 10/1995 | Atkinson et al. |
| 5,469,805 A | 11/1995 | Gibbs |
| 5,470,305 A | 11/1995 | Arnett et al. |
| 5,484,420 A | 1/1996 | Russo |
| 5,542,923 A | 8/1996 | Ensminger et al. |
| 5,545,150 A | 8/1996 | Danks et al. |
| 5,554,136 A | 9/1996 | Luther |
| 5,562,618 A | 10/1996 | Cai et al. |
| 5,571,093 A | 11/1996 | Cruz et al. |
| 5,575,769 A | 11/1996 | Vaillancourt |
| 5,624,395 A | 4/1997 | Mikhail et al. |
| 5,637,099 A | 6/1997 | Durdin et al. |
| 5,667,500 A | 9/1997 | Palmer et al. |
| 5,707,357 A | 1/1998 | Mikhail et al. |
| 5,743,873 A | 4/1998 | Cai et al. |
| 5,743,884 A | 4/1998 | Hasson et al. |
| 5,743,894 A | 4/1998 | Swisher |
| 5,752,928 A | 5/1998 | de Roulhac et al. |
| 5,752,938 A | 5/1998 | Flatland et al. |
| 5,803,078 A | 9/1998 | Brauner |
| 5,807,349 A | 9/1998 | Person et al. |
| 5,810,789 A | 9/1998 | Powers et al. |
| 5,843,044 A | 12/1998 | Moorehead |
| 5,853,397 A | 12/1998 | Shemesh et al. |
| 5,865,308 A | 2/1999 | Qin et al. |
| 5,944,698 A | 8/1999 | Fischer et al. |
| 5,984,902 A | 11/1999 | Moorehead |
| 5,989,233 A | 11/1999 | Yoon |
| 6,033,393 A | 3/2000 | Balbierz et al. |
| 6,045,734 A | 4/2000 | Luther et al. |
| 6,050,934 A | 4/2000 | Mikhail et al. |
| 6,056,717 A | 5/2000 | Finch et al. |
| 6,062,244 A | 5/2000 | Arkans |
| 6,092,551 A | 7/2000 | Bennett |
| 6,099,505 A | 8/2000 | Ryan et al. |
| 6,120,483 A | 9/2000 | Davey et al. |
| 6,152,129 A | 11/2000 | Berthon-Jones |
| 6,152,909 A | 11/2000 | Bagaoisan et al. |
| 6,167,886 B1 | 1/2001 | Engel et al. |
| 6,210,366 B1 | 4/2001 | Sanfilippo, II |
| 6,227,200 B1 | 5/2001 | Crump et al. |
| 6,270,489 B1 | 8/2001 | Wise et al. |
| 6,306,124 B1 | 10/2001 | Jones et al. |
| 6,364,861 B1 | 4/2002 | Feith et al. |
| 6,364,867 B2 | 4/2002 | Wise et al. |
| 6,375,637 B1 | 4/2002 | Campbell et al. |
| 6,436,077 B1 | 8/2002 | Davey et al. |
| 6,442,415 B1 | 8/2002 | Bis et al. |
| 6,446,671 B2 | 9/2002 | Armenia et al. |
| 6,508,791 B1 | 1/2003 | Guerrero |
| 6,551,270 B1 | 4/2003 | Bimbo et al. |
| 6,610,031 B1 | 8/2003 | Chin |
| 6,726,063 B2 | 4/2004 | Stull et al. |
| 6,786,884 B1 | 9/2004 | DeCant, Jr. et al. |
| 6,874,999 B2 | 4/2005 | Dai et al. |
| 6,929,631 B1 | 8/2005 | Brugger et al. |
| 6,953,450 B2 | 10/2005 | Baldwin et al. |
| 6,994,314 B2 | 2/2006 | Garnier et al. |
| 7,081,106 B1 | 7/2006 | Guo et al. |
| 7,252,652 B2 | 8/2007 | Moorehead et al. |
| 7,291,133 B1 | 11/2007 | Kindler et al. |
| 7,316,655 B2 | 1/2008 | Garibotto et al. |
| 7,435,236 B2 | 10/2008 | Weaver et al. |
| D595,846 S | 7/2009 | Racz et al. |
| D596,288 S | 7/2009 | Racz et al. |
| 7,601,141 B2 | 10/2009 | Dikeman et al. |
| 7,637,893 B2 | 12/2009 | Christensen et al. |
| 7,713,250 B2 | 5/2010 | Harding et al. |
| 7,731,700 B1 | 6/2010 | Schytte |
| 7,758,541 B2 | 7/2010 | Wallace et al. |
| 7,931,619 B2 | 4/2011 | Diamond et al. |
| 7,947,032 B2 | 5/2011 | Harding et al. |
| 7,951,121 B2 | 5/2011 | Weaver et al. |
| 7,988,679 B2 | 8/2011 | Daly et al. |
| 7,993,327 B2 | 8/2011 | Casey, II |
| D644,731 S | 9/2011 | Fangrow, Jr. |
| 8,034,035 B2 | 10/2011 | Weaver et al. |
| 8,079,987 B2 | 12/2011 | Moorehead et al. |
| 8,083,721 B2 | 12/2011 | Miller |
| 8,105,314 B2 | 1/2012 | Fangrow, Jr. |
| 2,720,881 A1 | 5/2012 | Murray |

(56) References Cited

U.S. PATENT DOCUMENTS

| | | |
|---|---|---|
| 8,187,234 B2 | 5/2012 | Weaver et al. |
| 8,257,321 B2 | 9/2012 | Lareau et al. |
| 8,328,768 B2 | 12/2012 | Quigley et al. |
| 8,337,470 B2 | 12/2012 | Prasad et al. |
| 8,343,113 B2 | 1/2013 | Hokanson |
| 8,377,011 B2 | 2/2013 | Weaver et al. |
| 8,398,607 B2 | 3/2013 | Fangrow, Jr. |
| 8,444,628 B2 | 5/2013 | Fangrow, Jr. |
| 8,454,574 B2 | 6/2013 | Weaver et al. |
| 8,454,579 B2 | 6/2013 | Fangrow, Jr. |
| 8,523,821 B2 | 9/2013 | Miller |
| 8,529,523 B2 | 9/2013 | Weaver et al. |
| 8,540,685 B2 | 9/2013 | Moorehead et al. |
| 8,585,660 B2 | 11/2013 | Murphy |
| 8,603,070 B1 | 12/2013 | Lareau et al. |
| 8,628,515 B2 | 1/2014 | Fangrow, Jr. |
| 8,679,074 B2 | 3/2014 | Daly et al. |
| 8,726,931 B2 | 5/2014 | Buiser et al. |
| 8,753,320 B2 | 6/2014 | Miller |
| 8,758,306 B2 | 6/2014 | Lopez et al. |
| 2,755,060 A1 | 7/2014 | Konno |
| 8,784,402 B1 | 7/2014 | Lareau et al. |
| 8,789,558 B2 | 7/2014 | Volker |
| 8,870,850 B2 | 10/2014 | Fangrow, Jr. |
| 8,876,797 B2 | 11/2014 | Lareau et al. |
| 8,926,571 B1 | 1/2015 | Keith |
| D722,155 S | 2/2015 | Wiegel et al. |
| D722,156 S | 2/2015 | Wiegel et al. |
| D722,157 S | 2/2015 | Wiegel et al. |
| 9,044,541 B2 | 6/2015 | Blanchard et al. |
| 9,186,494 B2 | 11/2015 | Fangrow |
| 9,192,753 B2 | 11/2015 | Lopez et al. |
| 9,192,755 B2 | 11/2015 | Ravenscroft |
| 9,205,243 B2 | 12/2015 | Lopez et al. |
| 9,206,283 B1 | 12/2015 | Santerre et al. |
| 9,238,129 B2 | 1/2016 | Fangrow, Jr. |
| D752,215 S | 3/2016 | Blennow et al. |
| 9,278,206 B2 | 3/2016 | Fangrow |
| D757,259 S | 5/2016 | Duck et al. |
| 2001/0023333 A1 | 9/2001 | Wise et al. |
| 2001/0037079 A1 | 11/2001 | Burbank et al. |
| 2002/0010425 A1 | 1/2002 | Guo et al. |
| 2002/0016584 A1 | 2/2002 | Wise et al. |
| 2002/0121530 A1 | 9/2002 | Socier |
| 2002/0156430 A1 | 10/2002 | Haarala et al. |
| 2002/0157664 A1 | 10/2002 | Fugelsang et al. |
| 2002/0165492 A1 | 11/2002 | Davey et al. |
| 2002/0193752 A1 | 12/2002 | Lynn |
| 2003/0122095 A1 | 7/2003 | Wilson et al. |
| 2004/0034324 A1 | 2/2004 | Seese et al. |
| 2004/0064128 A1 | 4/2004 | Raijman et al. |
| 2004/0102738 A1 | 5/2004 | Dikeman et al. |
| 2004/0108479 A1 | 6/2004 | Garnier et al. |
| 2004/0186444 A1 | 9/2004 | Daly et al. |
| 2004/0193119 A1 | 9/2004 | Canaud et al. |
| 2004/0210194 A1 | 10/2004 | Bonnette et al. |
| 2004/0267185 A1 | 12/2004 | Weaver et al. |
| 2005/0010176 A1 | 1/2005 | Dikeman et al. |
| 2005/0027261 A1 | 2/2005 | Weaver et al. |
| 2005/0043703 A1 | 2/2005 | Nordgren |
| 2005/0049555 A1 | 3/2005 | Moorehead et al. |
| 2005/0149116 A1 | 7/2005 | Edwards et al. |
| 2005/0165364 A1 | 7/2005 | DiMatteo et al. |
| 2005/0171488 A1 | 8/2005 | Weaver et al. |
| 2005/0171490 A1 | 8/2005 | Weaver et al. |
| 2005/0171510 A1 | 8/2005 | DiCarlo et al. |
| 2005/0283122 A1 | 12/2005 | Nordgren |
| 2006/0129092 A1 | 6/2006 | Hanlon et al. |
| 2006/0135949 A1 | 6/2006 | Rome et al. |
| 2006/0149189 A1 | 7/2006 | Diamond et al. |
| 2006/0149211 A1 | 7/2006 | Simpson et al. |
| 2006/0149214 A1 | 7/2006 | Breiter et al. |
| 2007/0161940 A1 | 7/2007 | Blanchard et al. |
| 2007/0161970 A1 | 7/2007 | Spohn et al. |
| 2007/0276313 A1 | 11/2007 | Moorehead et al. |
| 2008/0097341 A1 | 4/2008 | Casey |
| 2008/0108956 A1 | 5/2008 | Lynn et al. |
| 2009/0177187 A1 | 7/2009 | Weaver Quigley et al. |
| 2009/0292252 A1 | 11/2009 | Lareau et al. |
| 2011/0087093 A1 | 4/2011 | Buiser |
| 2011/0118612 A1 | 5/2011 | Miller |
| 2011/0264054 A1 | 10/2011 | Miller |
| 2011/0313367 A1 | 12/2011 | Daly et al. |
| 2011/0313368 A1 | 12/2011 | Weaver et al. |
| 2012/0271247 A1 | 10/2012 | Weaver et al. |
| 2012/0325351 A1 | 12/2012 | Volker |
| 2013/0060200 A1 | 3/2013 | Dalton et al. |
| 2013/0220462 A1 | 8/2013 | Lareau et al. |
| 2013/0338608 A1 | 12/2013 | Moorehead et al. |
| 2014/0081285 A1 | 3/2014 | Kucklick |
| 2014/0163516 A1 | 6/2014 | Lareau |
| 2015/0135554 A1 | 5/2015 | Smith |
| 2016/0008530 A1 | 1/2016 | Weaver et al. |
| 2016/0121041 A1 | 5/2016 | Weaver et al. |

FOREIGN PATENT DOCUMENTS

| | | | |
|---|---|---|---|
| DE | 20208420 | | 10/2002 |
| EP | 0128525 | | 12/1984 |
| EP | 0128625 | | 12/1984 |
| EP | 0198962 | | 10/1986 |
| EP | 0337617 | | 10/1989 |
| EP | 0366814 | | 5/1990 |
| EP | 0474069 | | 3/1992 |
| EP | 0864336 | | 9/1998 |
| EP | 0882466 | | 12/1998 |
| EP | 0930082 | | 7/1999 |
| EP | 1016431 | | 7/2000 |
| FR | 2508008 | | 12/1982 |
| FR | 2718969 | | 10/1995 |
| GB | 2102398 | | 2/1983 |
| WO | WO9206732 | | 4/1992 |
| WO | WO9516480 | | 6/1995 |
| WO | WO9617190 | | 6/1996 |
| WO | WO9623158 | | 8/1996 |
| WO | WO9723255 | | 7/1997 |
| WO | WO9726931 | | 7/1997 |
| WO | WO9822178 | | 5/1998 |
| WO | WO9942166 | | 8/1999 |
| WO | WO0006230 | | 2/2000 |
| WO | WO0044419 | | 8/2000 |
| WO | WO03084832 | | 10/2003 |
| WO | WO2005023355 | | 3/2005 |
| WO | WO2008051647 | | 5/2008 |
| WO | WO2009112838 | | 9/2009 |
| WO | WO2011008689 | | 1/2011 |
| WO | WO2011062767 | | 5/2011 |
| WO | WO2014014602 | | 1/2014 |
| WO | WO-2014153302 A1 * | 9/2014 | ............ A61M 39/24 |

OTHER PUBLICATIONS

Biffi, et al., A Randomized, Prospective Trial of Central Venous Ports Connected to Standard Open-Ended or Groshong Catheters in Adult Oncology Patients, American Cancer Society, pp. 1204-1212, date of 2001.

Hoffer et al., Peripherally Inserted Central Catheters with Distal versus Proximal Valves: Prospective Randomized Trial, Society of Interventional Radiology, pp. 1173-1177, vol. 12 No. 10, Oct. 2001.

McMahon, Evaluating New Technology to Improve Patient Outcomes, pp. 250-255, vol. 25, No. 4, Jul./Aug. 2002.

Carlo et al., A prospective Randomized Trial Demonstrating Valved Implantable Ports Have Fewer Complications and Lower Overall Cost Than Nonvalved Implantable Ports, pp. 722-727, date of 2004.

Burns, The Vanderbilt PICC Service: Program, Procedural, and Patient Outcomes Successes, pp. 1-10, vol. 10 No. 4, date of 2005.

Ricchezza et al., A Strategy for Reducing Catheter Occlusions and Infections: The Experience at St. Joseph's Hospital, 2009, date of 2009.

Ong et al., Prospective Randomized Comparative Evaluation of Proximal Valve Polyurethane and Distal Valve Silicone Peripherally Inserted Central Catheters, 1191-1196, Aug. 2010.

(56) References Cited

OTHER PUBLICATIONS

Aw et al., Incidence and Predictive Factors of Symptomatic Thrombosis Related to Peripherally Inserted Central Oatheters in Chemotherapy Patients, pp. 323-326, date of 2012.
Johnston et al., The Effect of Peripherally Inserted Central Catheter (PICC) Valve Technology on Catheter Occlusion Rates—The 'ELeCTRiC' Study, pp. 421-425, date of 2012.
Pittiruti et al., A Prospective, Randomized Comparison of Three Different Types of Valved and Non-Valved Peripherally Inserted Central Catheters, pp. 519-523, date of 2014.
International Search Report PCT-US-05-011244_ISR dated Jun. 6, 2005.
International Search Report PCT-US-05-000761_ISR dated Dec. 4, 2005.
International Search Report PCT-US-05-000761_WOSA dated Jul. 29, 2006.
International Search Report PCT-US-05-000761_IPRP dated Jul. 31, 2006.
International Search Report PCT-US-05-001244_IPRP dated Jul. 31, 2006.
International Search Report PCT-US-09-044468_ISR dated Dec. 23, 2009.
International Search Report PCT-US-10-041698_ISR dated Sep. 2009.
International Search Report PCT-US-09-044468_IPRP dated Nov. 23, 2010.
International Search Report PCT-US-09-044468_WOSA dated Nov. 25, 2010.
International Search Report 11158827_ESR dated May 11, 2011.
International Search Report 11158827-3_ESO dated May 19, 2011.
International Search Report PCT-US10-041698_IPRP dated Jan. 17, 2012.
International Search Report 10800375_SESR dated Jul. 10, 2014.
International Search Report 10800375-7_ESO dated Jul. 17, 2017.

* cited by examiner

A-A

A-A

BI-DIRECTIONAL, PRESSURE-ACTUATED MEDICAL VALVE WITH IMPROVED FLUID FLOW CONTROL AND METHOD OF USING SUCH

RELATED APPLICATIONS

This application claims the benefit of priority under 35 U.S.C. § 119(e) to U.S. Provisional Application No. 62/373,400, entitled "PICC or Port Bi-Directional Pressure-Actuated Valve" filed Aug. 11, 2016, which is hereby incorporated by reference in its entirety.

FIELD OF THE DISCLOSURE

This disclosure generally relates to a medical valve assembly for improved control of fluids and related methods of use, wherein the bi-directional, pressure-actuated valve assembly comprising a flexible diaphragm includes a first flow control portion permitting fluid to flow in a first direction when subjected to a first pressure threshold and a second control flow portion for permitting fluid to flow in a second direction when subjected to a second pressure threshold.

BACKGROUND OF THE INVENTION

Many medical procedures require repeated and prolonged access to a patient's vasculature for the delivery and/or exchange of drugs, blood products, nutritional fluids, or other fluids. Medical devices such as peripherally inserted catheters (PICCs), dialysis catheters, tunneled central catheters and subcutaneously implanted ports have been developed to ensure that a patient's peripheral vasculature does not sustain damage from repeated access. These long-term devices remain inserted in the patient's central vasculature for the duration of treatment protocols, which may last weeks, months or even years. It is medically desirable to manage fluid exchanges through these devices by controlling the fluid flow to prevent device complications such as fluid leakage and blood clotting. Clamps attached to the catheter shaft or extension tubing of the vascular access device have been employed to close of the fluid pathway when not in use. Using clamps has been shown to be problematic because the repeated pressure of the clamp against the tubing wall may weaken and damage the device tubing. Another problem with clamps the possibility of an incomplete tubing seal, which may result in the introduction of air into the fluid path and/or blood coagulation.

Based on the problems associated with clamps, bi-directional, pressure-activated valve assemblies have been incorporated into medical devices to provide required fluid flow control. These bi-directional, pressure-actuated valves generally include an elastic diaphragm or disk positioned within the device's fluid flow path that controls fluid flow through the device. The elastic diaphragm prevents inadvertent fluid flow when the device is not being used. The diaphragm may be a slitted, flexible membrane extending across a lumen, and generally constructed so that, when subjected to a fluid pressure of at least a threshold level, the edges of the slit separate from one another to form an opening through which fluid flows. When the pressure applied to the membrane drops below a predetermined threshold level, the slit closes to prevent fluid flow from or into the device. One such bi-directional, pressure-actuated valve assembly is described in U.S. Pat. No. 7,435,236 entitled Pressure-Actuated Valve with Improved Biasing Member, which is incorporated herein by reference.

One known design of a bi-directional, flexible diaphragm requires that the fluid pass through the same slit during both aspiration and infusion. The cracking pressure of such an elastic diaphragm is determined by the geometry of the valve housing components and how they mate with the peripheral part of the disk. A cracking pressure may be defined as the threshold pressure at which a fluid flow control portion of the diaphragm permits fluid to flow through the diaphragm. Thus, any adjustment of the fluid flow control portion, such as dimensions and slit geometry, influences fluid flow in both the injection and aspiration directions. Since it may be clinically desirable to have different cracking pressures for aspiration and injection, the design of the hub or other component which houses the disk must be dimensioned to account for two separate pressure differentials. Accordingly, there is a need for an improved bi-directional, pressure-actuated valve assembly having an elastic diaphragm that provides separate and independent injection and aspiration functions, each with unique cracking pressure.

Yet another problem with prior art pressure-actuated diaphragms is the increased probability of hemolysis during aspiration or infusion of blood. Hemolysis is the mechanical rupturing of red blood cells (erythrocytes) which causes the release of hemoglobin into the patient's circulatory system. Extracellular or "free" hemoglobin has been found to be associated with acute and chronic vascular disease, inflammation, thrombosis, renal impairment and other serious medical complications. Aspirating and infusing blood through a bi-directional slit valve results in shear forces and turbulence that may mechanically damage the erythrocytes and cause hemolysis. More particularly, as the blood is forced through the narrow slit of the diaphragm, the red erythrocytes are ruptured by the sharp edges of the slit. Accordingly, there is a need for a pressure-actuated, bi-directional valve assembly which minimizes the occurrence of hemolysis during blood infusion and aspiration.

Known methods of manufacturing an elastic diaphragm and housing assembly may be problematic, and result in high scrap rates. Typically, the valve is formed from a silicone sheet material which is punched to form the diaphragm with slit. The sheet material thickness and elastic modulus, both critical specifications to ensuring proper cracking pressures, are often inconsistent and may vary even within a single sheet. To address this problem, the sheet material undergoes a customized annealing process prior to punching the disks from the sheet. Due to the natural stretching of the disk material after assembly, the finished valve assembly is once again annealed to achieve the desired pressure actuation thresholds. These additional manufacturing and quality control steps result in a high scrap rate, long manufacturing cycles, inefficient production resource utilization and may have a negative impact on production responsiveness. Accordingly, there is a need for an improved valve assembly design which streamlines and shortens the manufacturing process, increases production throughput and more efficiently utilizes production resources.

BRIEF SUMMARY OF THE INVENTION

The following presents a simplified summary in order to provide a basic understanding of some novel embodiments described herein. This summary is not an extensive overview, and it is not intended to identify key/critical elements or to delineate the scope thereof. Its sole purpose is to present some concepts in a simplified form as a prelude to the more detailed description that is presented later.

According to at least one embodiment, a medical valve assembly for bi-directional fluid flow control is provided, comprising a first housing section and a second housing section, a diaphragm having a retention portion placed between the first housing section and the second housing section, a first fluid flow control portion, and a second fluid flow control portion. The first fluid flow control portion comprises a slit in the diaphragm permitting fluid to flow in a first direction when exposed to a first cracking pressure. The second fluid flow control portion comprises a first injection position which is in direct contact with the second housing section when fluid flows in a first direction, and a second injection position in which the second flow control portion is displaced from the second housing section when exposed to a second cracking pressure to permit fluid to flow in a second direction. The medical valve assembly may have the first direction of fluid flow comprising injection of the fluid through the diaphragm and the second direction of fluid flow comprising aspiration of the fluid through the diaphragm. The second fluid flow control portion of the diaphragm may further comprise at least one inter-spoke fluid communication channel between at least two spokes connecting the retention portion and the first fluid flow control portion. The second housing portion may further comprise a seating surface that contacts the second fluid flow control portion. The fluid may be power injected through the diaphragm at a flow rate of up to 5 mls/second. The first fluid flow control portion of the diaphragm may further comprise a dome which may extend in a proximal direction away from the second fluid flow control portion of the diaphragm. A slit may be located on an apex of the dome. The dome may comprise a fractional-cylinder outer profile.

According to at least one embodiment, a method for bi-directionally controlling fluid flow through a medical device is provided, comprising the steps of inserting a medical device into a patient, wherein the medical device comprises a housing comprising a first housing section and a second housing section, a diaphragm having a retention portion positioned between the first housing section and the second housing section, a first flow control portion, and a second flow control portion. The method may further comprise flowing a fluid in a first direction through the housing, wherein the first fluid flow control portion opens to permit fluid to flow through the diaphragm, and wherein the second fluid flow control portion is compressed against the second housing section to remain closed and prevent fluid to flow between the second fluid flow control portion of the diaphragm and the second housing section and flowing a fluid in a second direction through the housing, wherein the first fluid flow control portion remains closed, and the second fluid flow control portion is displaced away from the second portion of the housing to permit fluid to flow between the second fluid flow control portion and the second housing portion. The first direction of fluid flow may include the step of injecting fluid through the diaphragm and the second direction of fluid flow may include the step of aspirating fluid through the diaphragm. The medical device may be a PICC and the step of injecting fluid may include injecting fluid at a rate up to 5 mls/sec. The first fluid flow control portion may further comprise a dome and at least one slit along the dome. The second fluid flow control portion may further comprise at least two spokes forming at least one inter-spoke fluid communication channel through which fluid flows in the second direction. The method may further comprise the step of inserting a second medical device into the housing through the slit. The flow of fluid in a first direction may be at a lower rate than the flow of fluid in the second direction. The method may further comprise the step of flushing the housing after the step of flowing a fluid in a second direction through the housing. The second housing section may further comprise a seating surface to seat the second flow control portion against the second housing section to prevent fluid to flow between the second housing section and the second fluid flow control portion when flowing the fluid in the first direction through the housing. The dome may comprise a fractional-cylinder outer profile. The first fluid flow control portion may extend away from the second fluid flow control portion in a distal direction.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings.

DETAILED DESCRIPTION OF THE INVENTION

Figure 1:
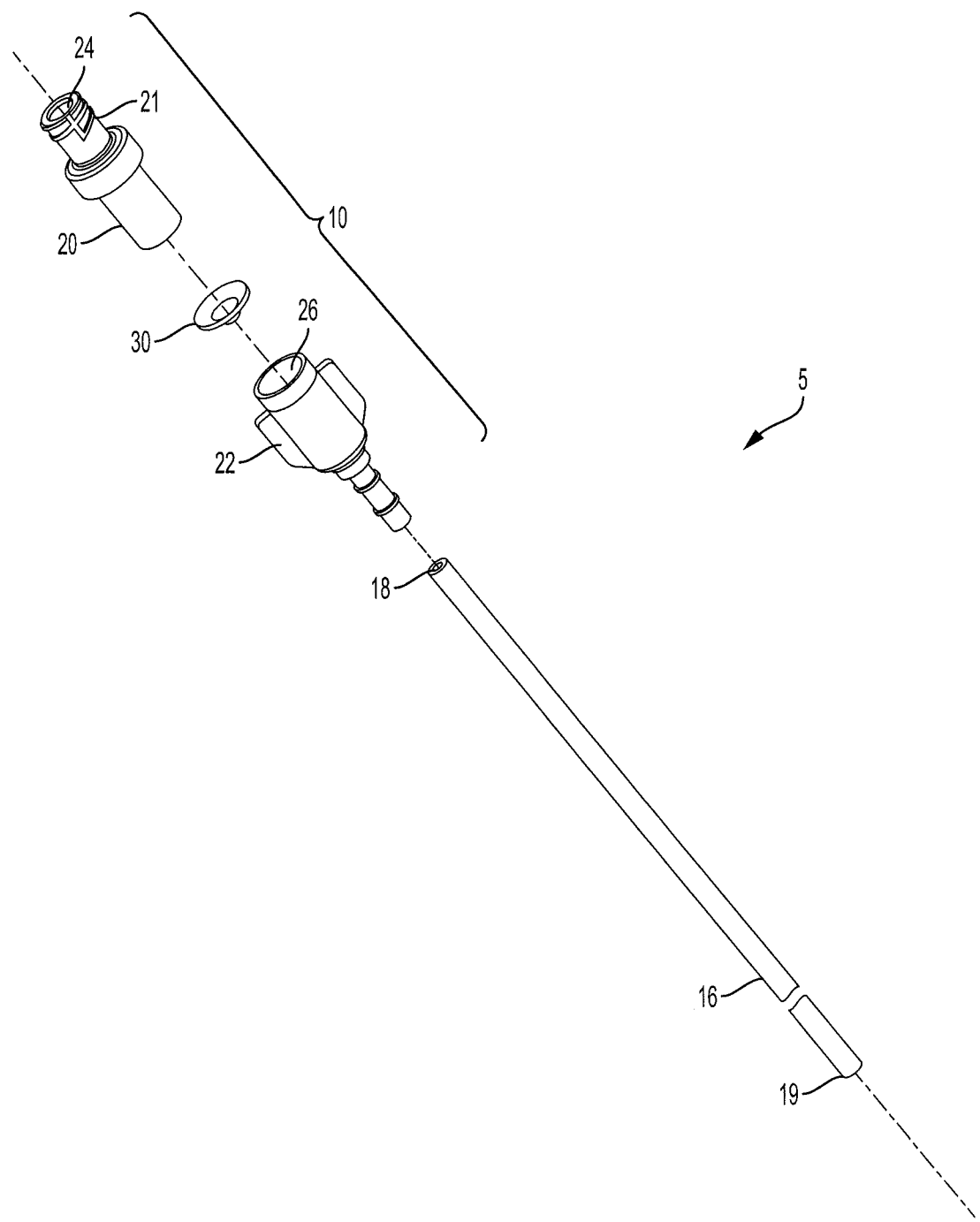
FIG. 1 depicts an exploded, isometric view of a catheter device illustrating an embodiment of a bi-directional, pressure-actuated valve assembly.

The present invention can be understood more readily by reference to the following detailed description and the examples included therein and to the Figures and their previous and following description. The drawings, which are not necessarily to scale, depict selected preferred embodiments and are not intended to limit the scope of the invention. The detailed description illustrates by way of example, not by way of limitation, the principles of the invention. As used herein, distal refers to a direction away from or distant from the point of reference, in this case the physician or user. Proximal refers to a direction toward or near to the physician or user. The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting.

Referring now in detail to the drawings, in which like reference numerals indicate like parts or elements throughout the several views, in various embodiments, presented herein is a bi-directional, pressure-actuated valve assembly for improved control of fluids and related methods of use.

Referring to FIG. 1, an exploded isometric view of a catheter device 5 is illustrated. The catheter 5 may be comprised of a catheter shaft 16 and a bi-directional, pressure-actuated valve assembly 10. Catheter shaft 16 includes a though lumen 18 extending from the medical valve assembly 10 to a distal tip 19. Valve assembly 10 may be comprised of a first housing section 20 including a first through lumen 24 and a second housing section 22 including a second through lumen 26. The first housing section 20 may include a connection element 21, such as a standard luer-type fitting for connection to other medical devices. A fluid flow path is defined by lumens 24, 26 and 18. Positioned between the first and second housing sections 20, 22 within the fluid flow path is a flexible diaphragm 30. Although the device illustrated in FIG. 1 is a catheter, the valve assembly 10 may be used in conjunction with various other vascular access devices including but not limited to dialysis catheters, subcutaneous ports, central venous lines, drainage catheters, and other long-term indwelling devices. Non-vascular access devices also fall within the scope of this invention including medical conduits for controlled fluid exchange such as urinary catheter and general drainage devices.

Figure 2:
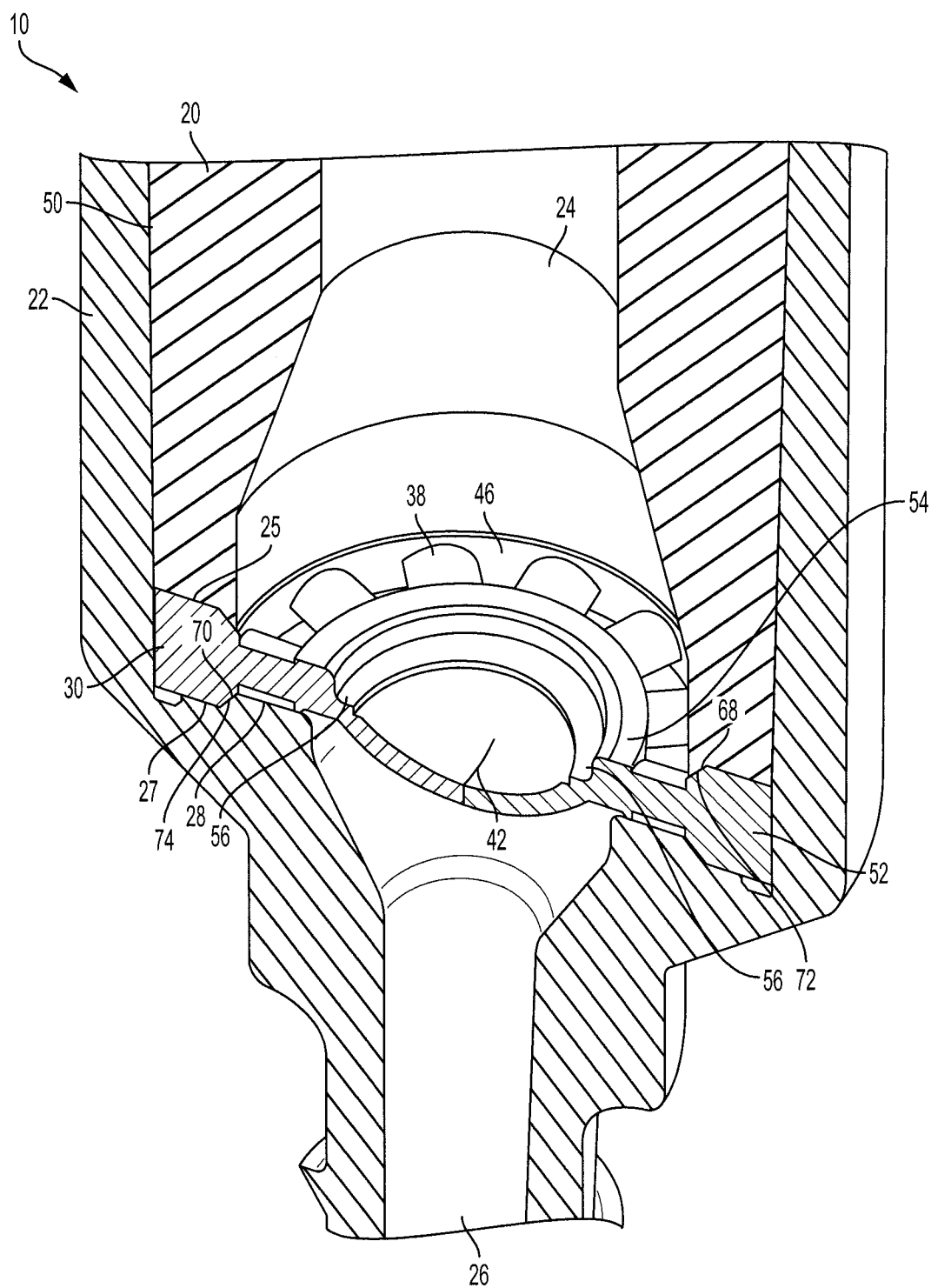
FIG. 2 illustrates an isometric partial cutaway of an embodiment of a bi-directional, pressure-actuated valve assembly.
Figure 3:
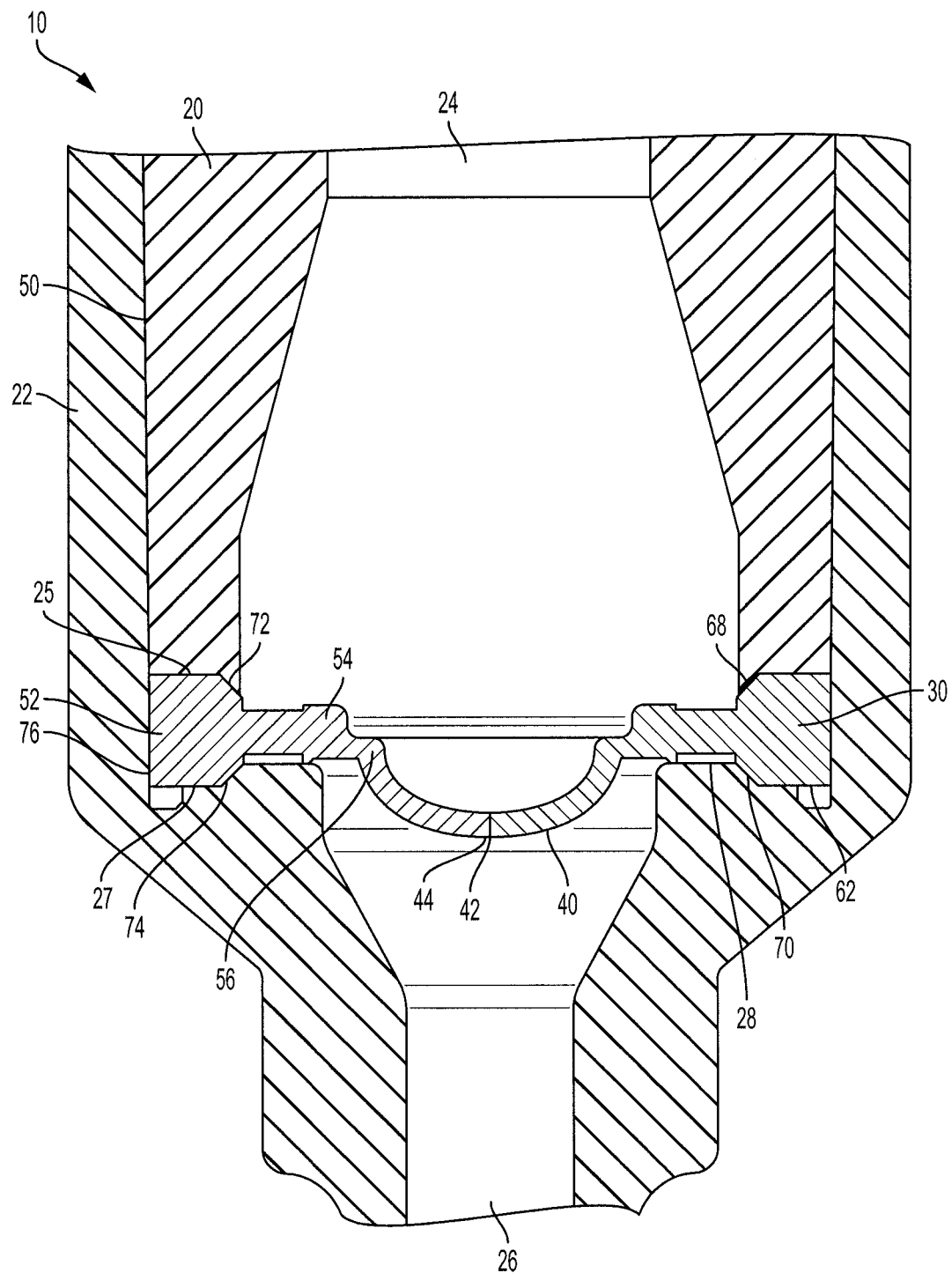
FIG. 3 depicts a partial cross-sectional view of an embodiment of a bi-directional, pressure-actuated valve assembly.

FIG. 2 and FIG. 3 illustrate an embodiment of a medical valve assembly 10 depicting flexible diaphragm 30 positioned within the assembly 10. Referring to both figures, a distal portion of first housing section 20 is shown partially positioned within second housing section 22. The housings may be comprised of a plastic-based material, metal or other materials known in the art. An adhesive or other bonding materials 50 may be used to permanently attach the two housing sections 20 and 22 together. Alternatively, housings sections 20 and 22 may be press fit together, or welded using known laser or ultrasound techniques, as commonly known in the art. In one embodiment, the housing can be a unitary structure, such as an injection molded hub. Flexible diaphragm 30 is captured and held securely in place between a first mating surface 25 of first housing section 20 and a second mating surface 27 of second housing section 22. As positioned, diaphragm 30 is situated perpendicularly across the longitudinal axis of the fluid flow path. The fluid flow path may be defined by lumen 24 of first housing section 20, a portion of lumen 26 of second housing section 22, and lumen 18 of catheter shaft 16 (see directional arrows of FIG. 6-FIG. 7). Flexible diaphragm 30 may include a dome 40 shaped portion. This dome 40 shaped portion may include an opening to permit fluid to flow through the diaphragm 30. The opening may include a slit 42. The slit 42 may be positioned in the center of the flexible diaphragm 30 or along any portion of the dome 40. At ambient, indwelling venous pressures, diaphragm 30 remains in a closed position, as illustrated in FIG. 2 and FIG. 3. Specifically, slit 42 of dome 40 is closed preventing fluid flow through the fluid flow path. As will be explained in more detail below, diaphragm 30 provides two separate fluid flow paths based on the pressure differential exerted on diaphragm 30 during aspiration and infusion of fluids.

Figure 4:
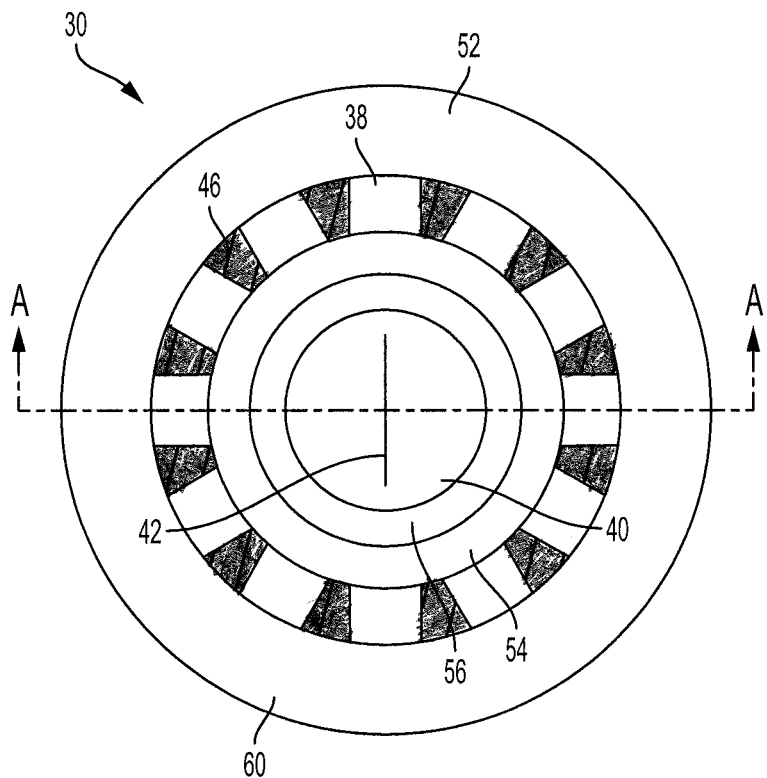
FIG. 4 illustrates a top down plan view of an embodiment of a flexible diaphragm.

Referring now to FIG. 4, a top down plan view of the flexible diaphragm 30 is illustrated. The diaphragm is preferably formed from silicone, because of that material's elasticity, compatibility with medical device applications, and its known capacity for being easily molded, even when molding extremely small parts. Other flexible synthetic rubbers or thermoplastic materials are also within the scope of this invention. Diaphragm 30 may have a circular profile and be comprised of an outer portion 52, a plurality of spokes 38 connecting the outer portion 52 to an intermediary portion 54, an inner portion 56 adjacent to and connecting with the intermediary portion 54, and a dome 40 extending distally from inner portion 56. In one non-limiting embodiment, the outer diameter of the diaphragm 30 is approximately 0.30", with an intermediary portion 54 diameter of 0.17" and an inner portion diameter of 0.13". Distally extending dome 40 includes a slit 42 which opens to allow fluid flow in a distal direction when exposed to a predetermined pressure threshold, as will be explained in more detail below. A plurality of inter-spoke fluid communication channels 46 formed between spokes 38 comprise a portion of a second fluid flow path allowing fluid to flow in a proximal direction when diaphragm 30 is exposed to a second predetermined pressure threshold.

Figure 4A:
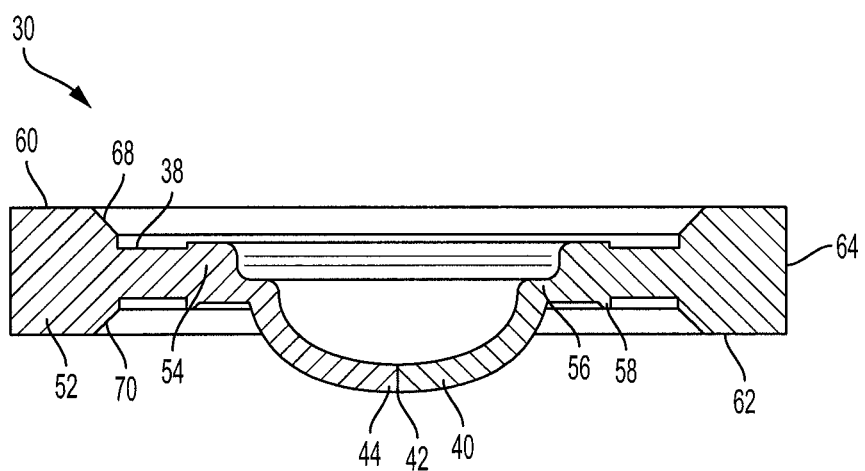
FIG. 4A illustrates a cross-sectional view of an embodiment of a flexible diaphragm taken along lines A-A of FIG. 4.

FIG. 4A illustrates a cross-sectional view of diaphragm 30 taken along lines A-A of FIG. 4. As shown, diaphragm 30 includes an outer portion 52 comprising a top surface 60, a bottom surface 62, and a side surface 64. Top and bottom outer surfaces, 60 and 62, include corresponding top and bottom chamfered surface sections 68 and 70. When the valve assembly 10 is assembled as shown in FIG. 2, flexible diaphragm 30 is subject to compressive forces along these multiple surfaces, ensuring that the diaphragm 30 is held in a sealed position between housing sections 20 and 22. The dispersion of compressive forces along these multiple surface areas prevents excessive compression in any one location of the flexible diaphragm 30, reducing the possibility of distortion of the diaphragm including inward bulging of the spokes 38 and/or dome 40. This multiple compression surface design also allows for high power injections through the device without risking displacement of the diaphragm 30 within the valve assembly 10. In one example, radiographic contrast dye may be injected at a rate of up to 5 ml/sec with power injection pressure settings of up to 325 PSI.

The outer portion 52 of diaphragm 30 is also held in a compressed state by both the first mating surface 25 of first housing section 20 and the second mating surface 27 of second housing section 22, as shown in FIG. 2 and FIG. 3.

As a non-limiting example, the height of the outer portion of diaphragm 30 prior to assembly with the two housing sections 20 and 22 may be 0.050". Once assembled within the first and second housing sections, 20 and 22, the compressive forces against diaphragm 30 cause the outer portion 52 height to be reduced to between 0.040" to 0.045", in one non-limiting example. The first housing may comprise a first chamfer 72 and second housing 22 may comprise a second chamfer 74, such that compressive forces are directed outwardly away from the longitudinal axis of the fluid flow path. Outer portion side surface 64 of diaphragm 30 also undergoes compression against an inner wall 76 of the second housing. The inwardly angled surfaces of top and bottom chamfers 68 and 70 of flexible diaphragm 30 correspond to and are dimensioned to mate with the two inwardly angled surfaces of first and second chamfers 72 and 74 (see FIG. 2 and FIG. 3) of the first and second housing sections 20 and 22. In one non-limiting embodiment, diaphragm chamfers 68, 70 extend at a 45 degree angle toward the central longitudinal axis of fluid flow path and first and second housing chamfers 72 and 74 extend away from the central longitudinal axis of the flow path at 45 degree angles. During the manufacturing process, the second chamfered surface 74 and second mating surface 27 of the second housing section 22 together provide an area upon which diaphragm 30 is positioned prior to insertion of first housing section 20, thus ensuring that flexible diaphragm 30 remains centered during subsequent assembly steps. As diaphragm 30 is compressed between housing sections 20 and 22, the mated chamfered surfaces 72 and 74 cause the displacement of the bi-directional, diaphragm material to be directed outwardly toward the housing luminal walls rather inwardly toward the spokes 38 and intermediary portion 54. Although the chamfered surfaces described above are said to be at a 45-degree angle, other angles and profiles including radiused surfaces are within the scope of this invention.

Figure 8:
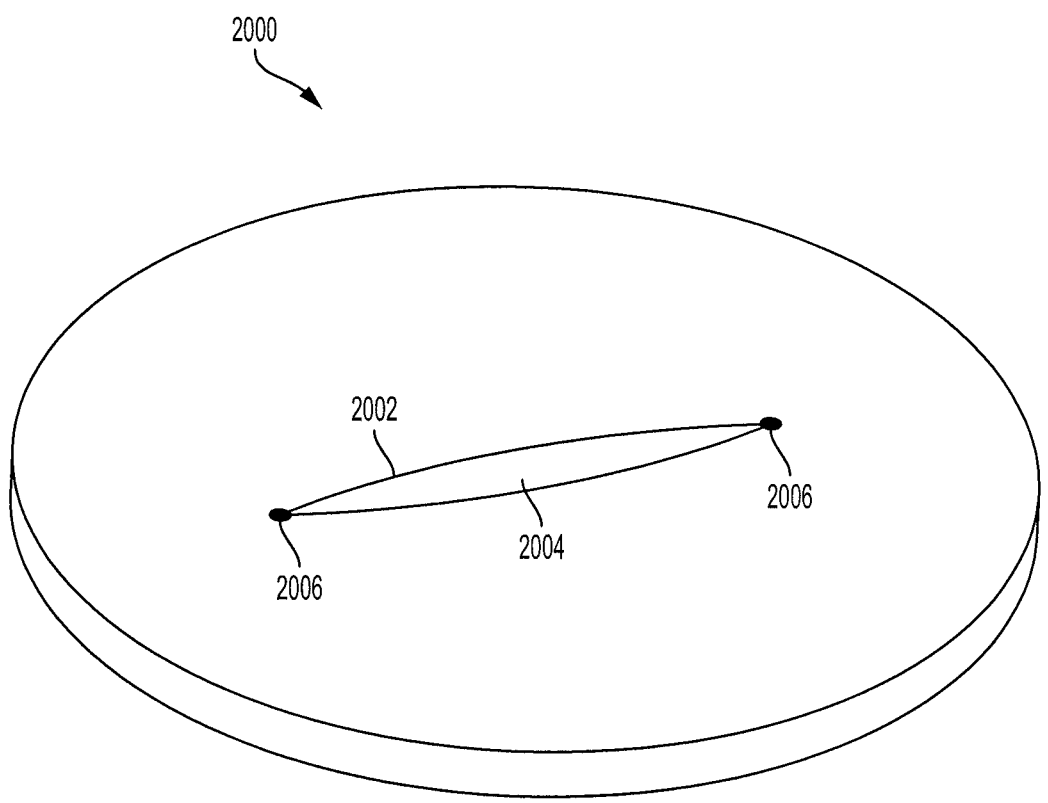
FIG. 8 illustrates an isometric plan view of a diaphragm of the prior art.

Thus, unlike prior art flat diaphragms, as shown in FIG. 8, which have at most three compressive surfaces, diaphragm 30 of the invention described herein is held securely in place by the compressive forces on five separate surfaces of the outer portion 52, thus providing a more robust, secure assembly. These combined compressive surfaces of housing 20 and 22 form a retention portion of the bi-directional, pressure-actuated valve assembly 10. The compressed surfaces of the outer portion 52 include top and bottom surfaces 60 and 62, side surface 64, and upper and lower chamfered surfaces 68 and 70. The enhanced securement created from these multiple compression areas allows the user to perform high-pressure, high-velocity infusions and aspirations through the diaphragm without causing damage or dislodgement. The design also is advantageous in that the bi-directional, pressure-actuated functional components of the diaphragm, namely the dome/slit, annular projection, and spokes, which form the fluid channels through the diaphragm 30, are not deformed because of compressive forces on the diaphragm, since material displacement caused by constriction of retention portions of diaphragm 30 is biased outwardly from the central longitudinal axis of the medical device.

Still referring to FIG. 4 and FIG. 4A, extending inwardly from outer portion 52 are a plurality of spokes 38 which connect the outer portion 52 to the intermediary portion 54. Optionally, diaphragm 30 may be comprised of the outer and intermediary portions only. Spokes 38 may be of a reduced height relative to both the outer and intermediary portions 52 and 54. In one non-limiting embodiment, spokes 38 may be approximately 0.021" in height, may be from two to twenty in number, and be separated from each other by inter-spoke fluid communication channels 46. Spokes 38 may have radiused outer profiles to minimize damage to red blood cells. In one non-limiting embodiment, the total area between the spokes which form the inter-spoke fluid communication channels 46 is $0.0048"^2$.

Intermediary portion 54 includes annular projection 58 extending distally from the bottom surface of portion 54. Annular projection 58 extends along the entire periphery of intermediary portion 54 and in one example, projection 58 may have a diameter of 0.168" and a circumference of 0.528". When exposed to normal venous pressures, annular projection 58 is in sealing contact with seating surface 28 of the second housing section 22. A slight amount of compression of annular projection 58 during a resting state is desirable to ensure no fluid leakage occurs between projection 58 and seating surface 28 during ambient pressure conditions. As will be explained in greater detail below, when exposed to a predetermined fluid pressure threshold, annular projection 58 becomes displaced and moves out of contact with seating surface 28, thus creating a fluid flow channel between second housing section lumen 26, inter-spoke fluid communication channels 46 and first housing section lumen 24. Still referring to FIG. 4A, flexible diaphragm 30 includes an inner portion 56 extending inwardly from intermediary portion 54 and integrally connected to dome 40. In a non-limiting embodiment, inner portion 56 may be approximately 0.012" in width and 0.010" in height. Dome 40, which may be 0.105" in diameter, includes a slit 42 extending completely through dome 40 wall at dome apex or crown 44. Other slit configurations and locations are within the scope of this invention, including a plurality of slits arranged in a parallel or non-parallel relationship, non-linear slits, and intersecting slits (not shown). In one non-limiting example, dome 40 may have a curvature defined by a radius of 0.100" or less to facilitate introduction of a guidewire or another medical accessory through the slit 42. When dome 40 is exposed to predetermined pressure threshold, longitudinal slit 42 of dome 40 opens to create a distal fluid flow channel between second housing section lumen 26 and first housing section lumen 24 through the space created by the separation of the dome walls at slit 42.

Figure 6:
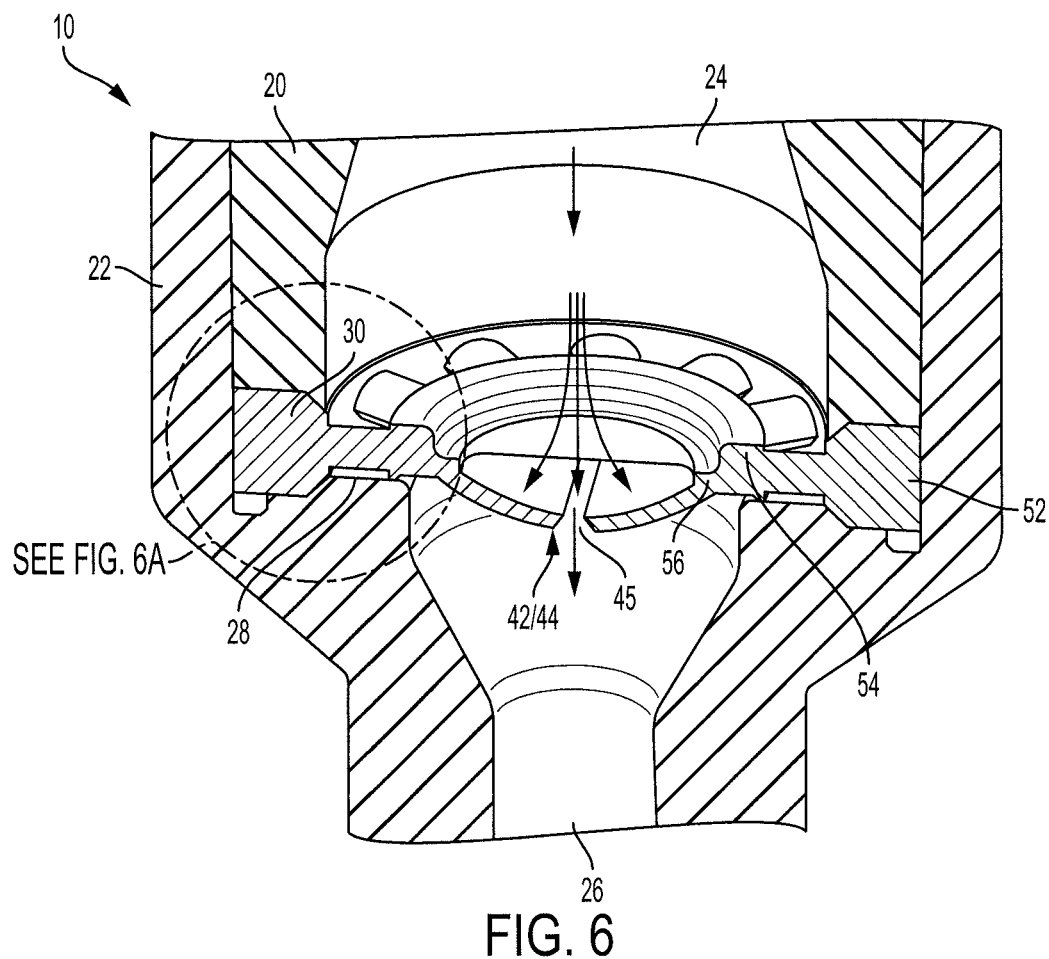
FIG. 6 illustrates an isometric partial cutaway of an embodiment of a bi-directional, pressure-actuated valve assembly depicting a first fluid flow through the diaphragm.

One key advantage of the inventive bi-directional, pressure-actuated valve assembly 10 described herein is the provision for separate and exclusive directional fluid flow channels through flexible diaphragm 30, which may include a first fluid control portion and second fluid control portion. FIG. 6 illustrates an isometric partial cutaway of an embodiment of the valve assembly 10 depicting a first fluid control portion through the flexible diaphragm 30. As depicted by directional arrows, fluid flows in first direction, such as during an injection or infusion into the body, under pressure through the first housing section lumen 24. When the fluid pressure applied to the dome 40 reaches a pre-determined, first cracking value, slit 42 opens creating a slit gap 45, through which fluid flows distally into the second housing section lumen 26.

The first cracking threshold of the flexible diaphragm during fluid flow in a first direction may vary based on the physical attributes of flexible diaphragm 30 and the desired clinical application. In one non-limiting example, a first cracking pressure may be between 25 and 32 mmHg. This range is normally desirable to accommodate slower gravity-fed infusion procedures, such as intravenous therapy in which a fluid source such as a saline bag is positioned 1-3 feet above the patient. It is desirable that the flexible diaphragm valve 30 remain in an open, first position permitting fluid to flow through valve 30 slit gap 45 until the fluid source is almost empty, at which point the pressure drop should fall below the first minimum cracking pressure of the diaphragm causing slit 42 to close, preventing further fluid flow.

Figure 6A:
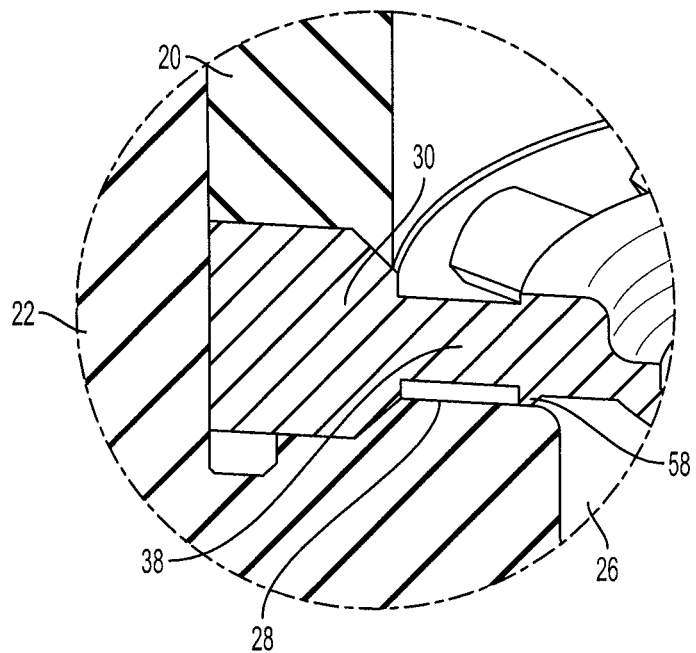
FIG. 6A is an enlarged, partial isometric view of portion of the valve assembly portion taken from the enlarged circled area of FIG. 6 illustrating a closed first fluid flow path.

FIG. 6A shows an enlarged partial view of FIG. 6, illustrating details of a flexible diaphragm 30 with second fluid flow path in a closed position, in which fluid is prevented from flowing proximally through the diaphragm. As shown, annular projection 58 is securely seated on seating surface 28 of second housing section 22. Annular projection 58, in a compressed state, seals against seating surface 28 and thus prevents any fluid from flowing through the second fluid flow path during infusion of fluids through the diaphragm.

Figure 7:
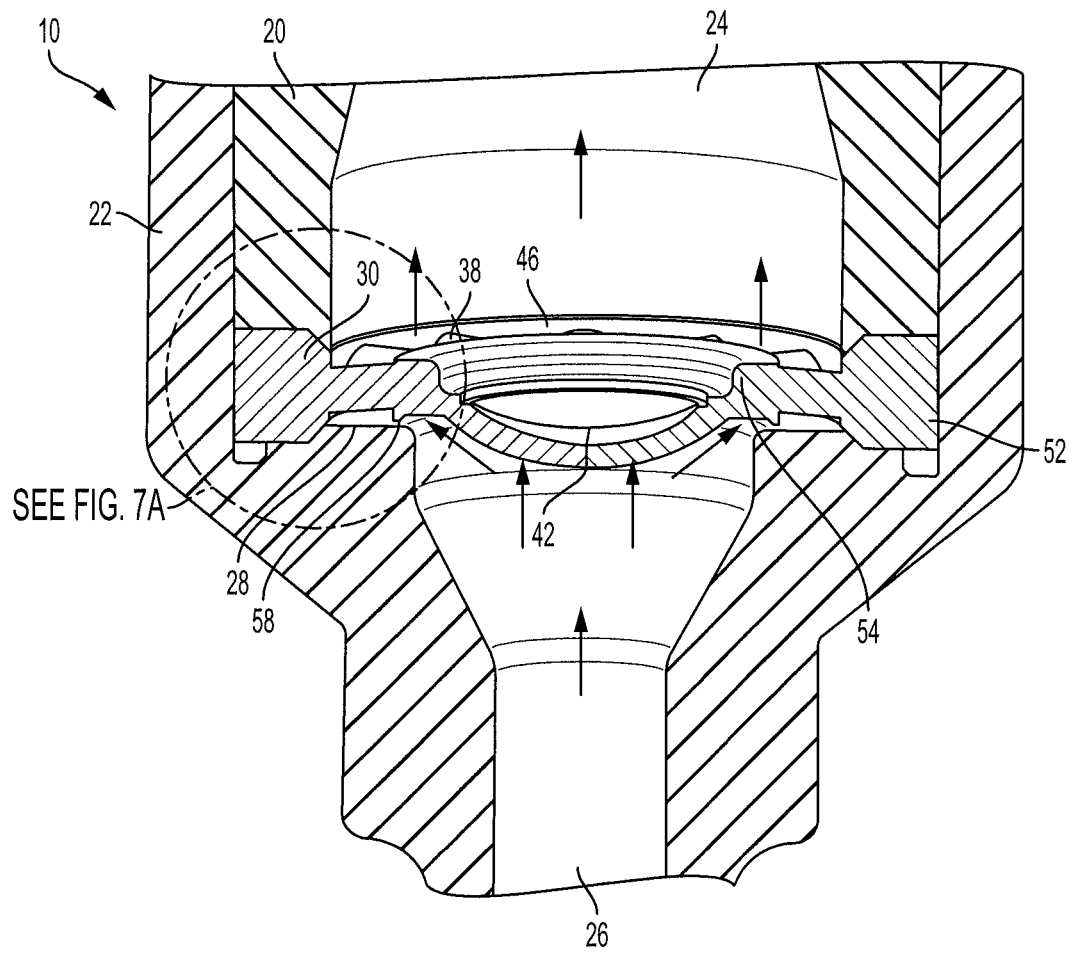
FIG. 7 illustrates an isometric partial cross-section of an embodiment of valve assembly depicting a second fluid flow through the diaphragm.
Figure 7A:
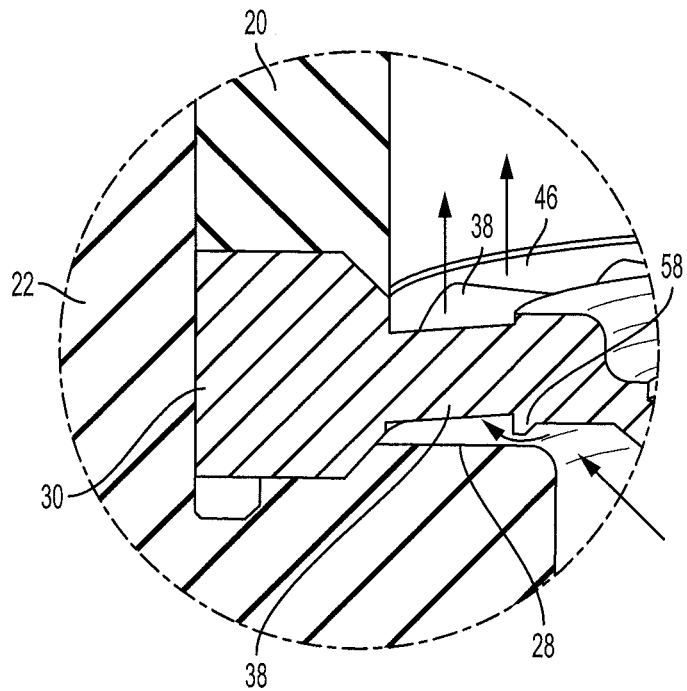
FIG. 7A is an enlarged, partial isometric view of a portion of the valve assembly taken from the enlarged circled area of FIG. 7 illustrating an open second fluid flow path.

FIG. 7 illustrates an isometric partial cutaway of an embodiment of the bi-directional, pressure-actuated valve assembly 10 depicting a second fluid control portion through diaphragm 30. FIG. 7A show an enlarged partial view of FIG. 7, illustrating details of a second fluid flow path during fluid flow in a second direction, such as during aspiration from a patient's body. As depicted by directional arrows, fluid flows under pressure through the catheter shaft 16 into second housing section lumen 26 to the flexible diaphragm 30. When the fluid pressure being exerted against diaphragm 30 reaches a pre-determined cracking pressure, dome 40, inner portion 56, intermediary portion 54 and spokes 38 are displaced upwardly (proximally) toward first housing lumen 24. The upward flexing of flexible diaphragm 30 causes annular projection 58 to become unseated and move out of contact with seating surface 28 of second housing section 22, creating a channel for fluid flow in a second direction through the space between the bottom surface of intermediary portion 54 and seating surface 28, as indicated by the directional arrows FIGS. 7 and 7A. In one non-limiting example, the height of upward displacement of the annular projection from the seating surface 28 may be between 0.010" and 0.020". The spokes 38 will also be displaced such that the spoke is no longer in parallel alignment with seating surface 28 (see FIG. 7A). Fluid will continue to flow in a second direction, passing through the plurality of inter-spoke fluid communication channels 46 into the first housing section lumen 24. In one non-limiting embodiment, fluid may then flow into the aspiration source such as a syringe or accessory dialysis tubing.

The cracking pressure for opening the second fluid control path for flowing fluid in a second direction may vary based on the physical attributes of flexible diaphragm 30 and the desired clinical application. For example, the cracking pressure may be between 40 and 90 mmHg. The actuation pressures during fluid flow in a second direction compared with a lower first cracking pressure of fluid flow in a second direction, provides additional protection against leakage of fluids present in the catheter shaft between medical procedures. A pressure threshold within these ranges is normally desirable to accommodate syringe aspiration procedures, which can create a differential pressure that far exceeds normal blood pressure ranges.

Thus, in one key aspect of the inventive concepts disclosed herein, the flexible diaphragm provides separate and exclusive first and second fluid flow paths, thereby allowing for independent customization of desired cracking pressures for opposite flow directions. Unlike prior art valve assemblies having a single, pressure-actuated slit through which both aspiration and infusion fluids flow, diaphragm 30 provides exclusive flow passages dedicated to each flow direction. As such, the physical diaphragm characteristics and geometries which control directional flow characteristics may be separately adjusted to achieve a specific pressure threshold and/or flow rate for each fluid flow direction. For fluid flow in a first direction, such as for infusion of fluids, these characteristics include but are not limited to dome 40 height and thickness, slit 42 length and inner portion 56 profile, all of which affect the first cracking threshold during fluid flow in first direction. The customization of these features will have no effect on the diaphragm's capacity to flow fluid in a second direction since the first fluid flow channel remains closed during flow in a first direction, such as infusion. For flowing fluid in a second direction, such as for aspiration, these characteristics include, but are not limited to, customization of geometries, contours and number of spokes 38, inter-spoke fluid communication channels 46, inner, intermediary and outer portions 56, 54, 52 and annular projection 58. As an example, reducing the number and/or dimensions of spokes 38 would decrease the amount of force required to displace annular projection 58 and increase flow rates through the diaphragm during fluid flow in a second direction since the total area of inter-spoke fluid communication channels increases. In consequence, the pressure threshold needed to actuate the second flow channel would be lowered. Customization of individual fluid flow features will have no effect on the flexible diaphragm's first cracking threshold since the first fluid flow channel (specifically slit 42) remains closed flow in a second direction.

In yet another advantage of the invention disclosed herein, the unique design of the flexible diaphragm 30 reduces the probability of hemolysis during both infusion and aspiration of blood, when compared with prior art bi-directional, pressure-actuated valves with slit configurations. Blood infusion or reinfusion is routinely performed through vascular access devices including dialysis catheters, PICCs, ports and central venous lines. Medical procedures requiring significant volume blood exchanges include, but are not limited to apheresis and dialysis.

Referring to FIG. 8, which illustrates a prior art slit valve 2000 in an open or pressure-actuated state, wherein the profile of the slit opening 2002 is widest at the center 2004 of the disk, becoming narrower as the slit extends outwardly to the slit terminal ends 2006. As the blood is infused through the narrow slit opening 2002, the red blood cells pass through the slit opening where they become susceptible to rupture when they contact the edges of the slit 2002 walls, particularly in the peripheral areas and terminal ends 2006 of the slit, where the gap through which blood passes is narrowest. Additionally, as more blood is forced through the slit, the material stretches from the pressure, causing the slit edges to become tauter and the opening 2002 narrower, thereby increasing number of red blood cells exposed to damage. As an example, the slit opening 2002 may be 0.115" in length with a maximum gap opening of 0.006" at the center point 2004 tapering down to 0.001" at slit terminal ends 2006, with a total fluid flow area through slit opening 2002 is approximately $0.00034"^2$.

Figure 9:
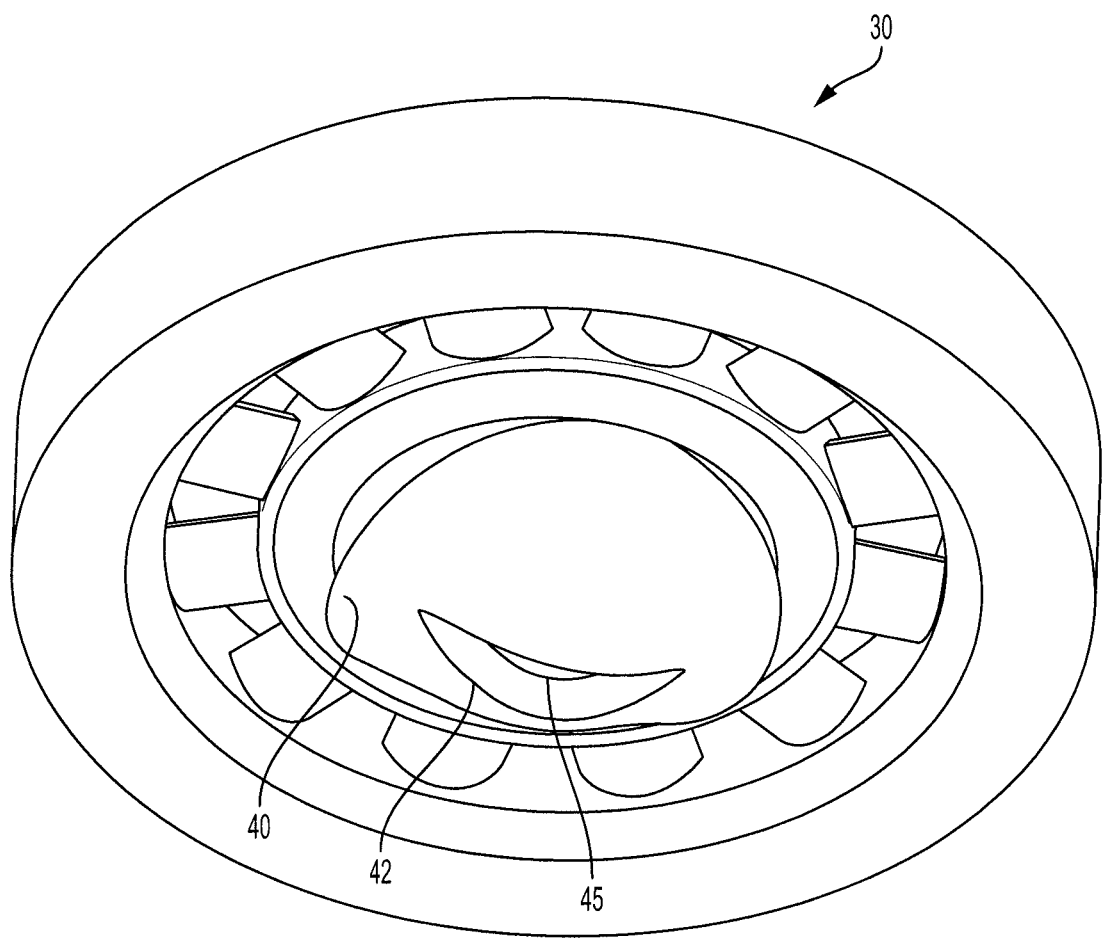
FIG. 9 depicts an isometric view of a flexible diaphragm in a fully open first fluid flow position.

In contrast, during infusion through the valve assembly 10 shown in FIG. 6 and FIG. 9, the occurrence of hemolysis is mitigated by the domed design of flexible diaphragm 30. As previously described, blood flows through the first fluid pathway through the slit 42, as with the prior art slit device of FIG. 8. At ambient pressures, dome 40 of diaphragm 30 is in a relaxed, non-stretched position and accordingly is more pliable. The more flexible nature of the dome 40, particularly at apex 44 where the slit 42 is positioned, provides a flow path which is less likely to damage red blood cells. In addition, the dome shape creates a rounder, wider slit gap 45 because of the way that the dome side walls can flex when under pressure. This flexibility is not present in the prior art flat disk configurations. Flexible membrane 30 has a much wider maximum gap opening during fluid flow in a first direction. Accordingly, hemolysis is less likely to occur through flexible diaphragm 30 than prior art slit valve 2000.

It is well known that increasing the velocity of blood withdrawal has a direct impact on hemolysis rates. Faster flow rates may increase red blood cell damage. In comparison to the FIG. 8 prior art slit valve design, the flexible diaphragm 30 provides an second fluid path capable of accommodating a much larger fluid volume, whereby reducing the occurrence of hemolysis. Referring specifically to FIG. 3 and FIG. 7, annular projection 58 of intermediary portion 54 is in sealing contact with seating surface 28 of second housing section 22 when not subject to aspiration pressures. In one non-limiting example, flexible diaphragm 30 includes an annular projection 58 having a diameter of 0.168" and a corresponding circumference of 0.528" as previously described. Using an equivalently sized prior art disk with a slit length of 0.150", the gap length available for fluid flow is only 28% of the gap length available through the annular projection 58. Because the area of the resultant gap created by displacement of annular projection 58 is much larger than the area of a slit disk design, a larger volume of blood will pass through the flexible diaphragm 30 compared with the prior art design. In other words, to attain equivalent flow volumes, rate of blood flow through prior art valve must be much higher than the rate required for diaphragm 30. Accordingly, use of the flexible diaphragm design described herein will reduce hemolysis rates by lowering the blood flow velocity while still achieving clinical blood volume requirements.

If higher aspiration flow rates are necessary for a medical procedure, the flexible valve 30 described herein performs in a superior manner relative to prior art pressure-actuated valves. Specifically, if the withdrawal rate is increased, the increased pressure exerted against the exposed underside of diaphragm 30 results in a further upward displacement of portions of the diaphragm elements, including the dome 40, inner portion 56, intermediary portion 54, spokes 38 and annular projection 58. This movement creates an even larger annular gap through which more blood volume can flow. In comparison, any increase in withdrawal rates against a prior art valve as shown in FIG. 8, will further stretch the disk and slit, increasing material tension along the edges of the slit 2002 of the slit valve 2000. As previously mentioned, these sharp edges may increase the likelihood of hemolysis.

Figure 5:
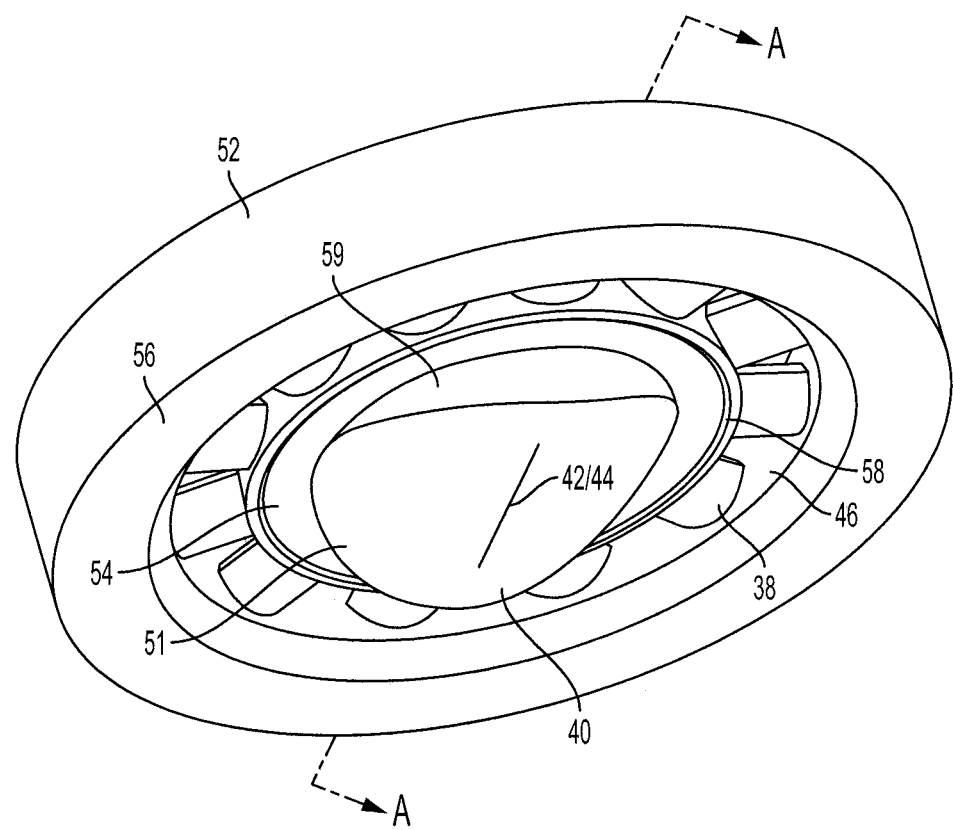
FIG. 5 depicts an isometric plan view of an embodiment of a flexible diaphragm.
Figure 5A:
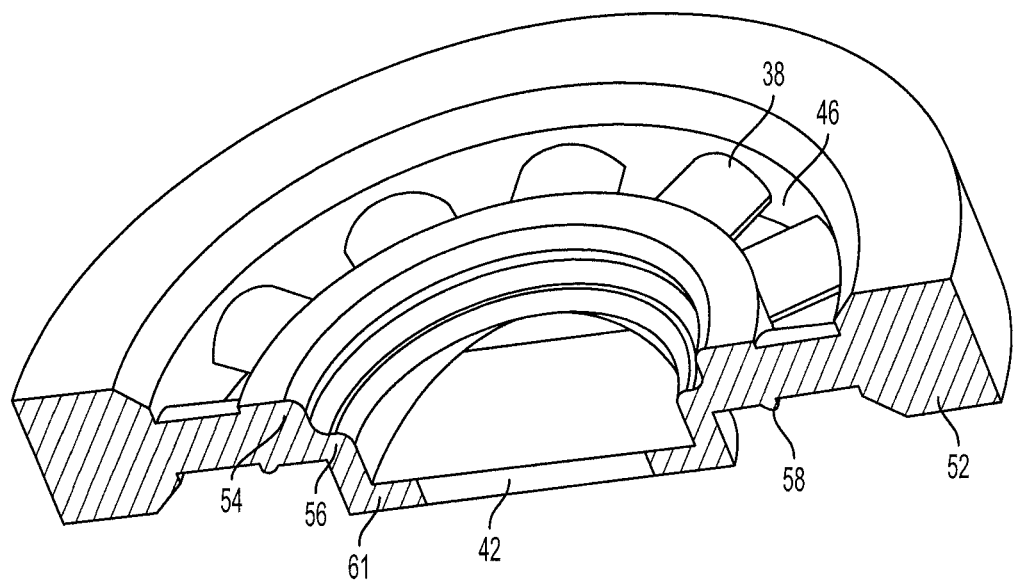
FIG. 5A illustrates an isometric cross-sectional view of an embodiment of a flexible diaphragm, taken along lines A-A of FIG. 5.

In one embodiment, flexible diaphragm 30 may include a first fluid flow control portion having a geometric design comprising a partial dome with a fractional-cylinder outer profile, as shown in FIG. 5 and FIG. 5A. FIG. 5 illustrates an enlarged, isometric, distal-facing view of diaphragm 30. As with other described embodiments, diaphragm 30 includes an outer portion 56, and an intermediary portion 54 connected to the inner portion 56 by a plurality of spokes 38 which form a plurality of inter-spoke fluid communication channels 46. Annular projection 58 extends distally from intermediary portion 54 and forms part of second fluid control portion. Extending distally from inner portion 56 is dome 40 having a base wall 51 with fractional-cylinder profile. Base wall 51 is attached to side walls 59 which extend from base wall 51 to intermediary portion 54. In one non-limiting embodiment, side walls 59 may be approximately 0.022" in length.

FIG. 5B depicts an isometric, cross-sectional view of flexible diaphragm 30 taken along lines A-A of FIG. 5A. When cut along lines A-A of base wall 51, the bottom surface 61 is planar and does not have a curvature. Slit 42 is formed in planar surface 61 in line with apex 49 of base wall 51. The base wall design of dome 40 has several advantages. In one such advantage, forming the slit 42 in dome 40 is simpler from a manufacturing perspective relative to a standard dome shape because the slit 42 is formed in planar surface 61 rather than through a curved wall of a dome. In yet another advantage, the straight side walls 59 attached to base wall 51 provide additional structural strength when diaphragm 30 is subjected to high infusion and aspiration pressures, thereby preventing distortion and possible partial collapse of the dome 40.

Figure 10A:
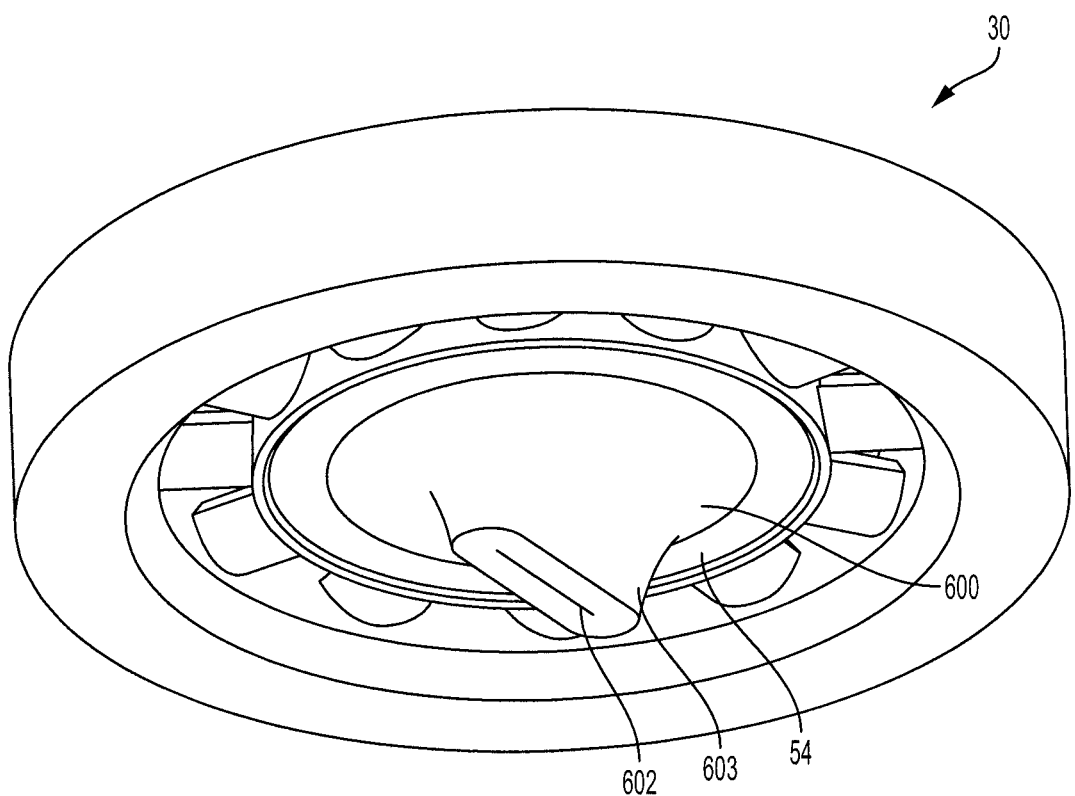
FIG. 10A depicts an isometric view of an alternate embodiment of a diaphragm shown in a closed position.
Figure 10B:
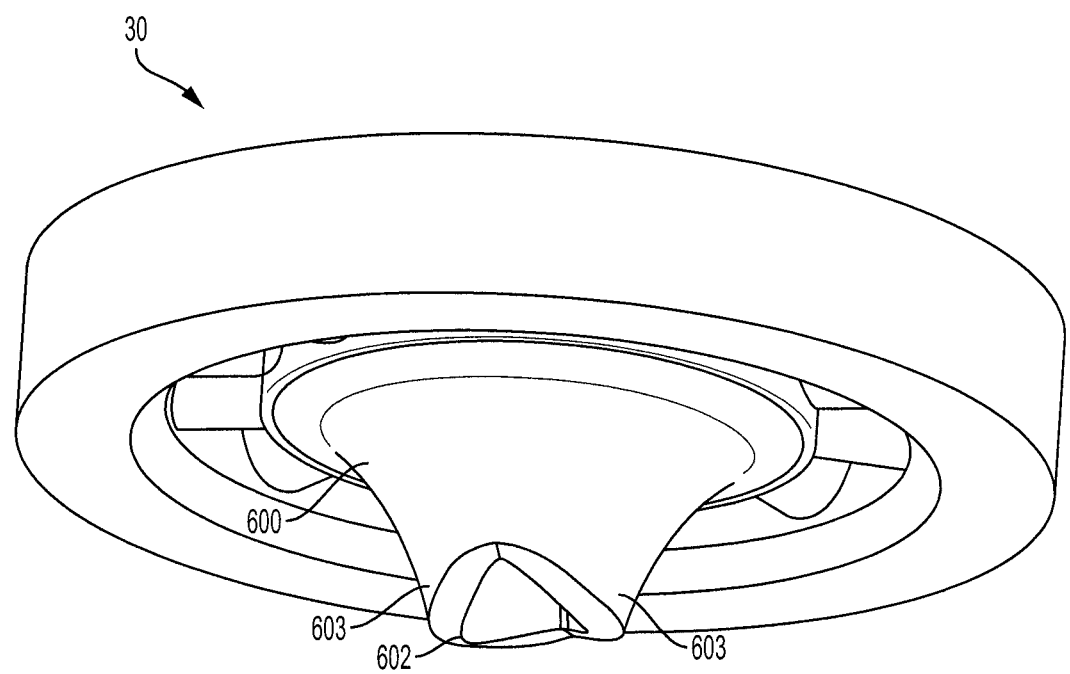
FIG. 10B depicts an isometric view of the diaphragm of FIG. 10A shown in an open position.

In an additional embodiment, flexible diaphragm valve 30 may include a one-way duckbill infusion valve 600 in place of dome 40 and slit 42, as illustrated in FIG. 10A and FIG. 10B. As is known in the art, a one-way duckbill may be described as a one-piece, elastomeric component comprising a one-way pressure-actuated valve element in a normally closed position. The pressure-actuated valve is designed to open in response to a predetermined pressure to allow fluid to flow through the valve.

As part of the embodiment of FIG. 10A and FIG. 10B, one-way duckbill infusion valve 600 is integrally connected to and extends distally from inner portion 56. Alternatively, one-way duckbill infusion valve 600 may be connected to intermediary portion 54. The second fluid flow control portion for aspiration of flexible diaphragm 30 operates as described previously. Duckbill infusion valve 600 includes a central slit opening 602 positioned at the distal end of the diaphragm. One-way duckbill valve 600 may be formed as part of the injection molding process previously described. The flexible diaphragm 30 remains in a closed position when exposed to ambient pressures, as illustrated in FIG. 10A. One-way duckbill valve 600 acts as a first fluid flow conduit allowing fluid to flow in a first direction through central slit opening 602 when diaphragm 30 is exposed to a predetermined pressure threshold, as shown in FIG. 10B. In one advantage of this embodiment, flexible diaphragm 30 may accommodate a larger volume of fluid flow through the duckbill valve 600 during infusion since the fluid pathway formed by outward flexing of the duckbill valve sidewalls 603 covers a much larger cross-sectional area than the area created by the opening of prior art valve of FIG. 8. The larger cross-sectional opening of the duckbill valve component 600 when actuated not only allows for higher fluid flow rates but also reduces the occurrence of hemolysis.

Figure 11:
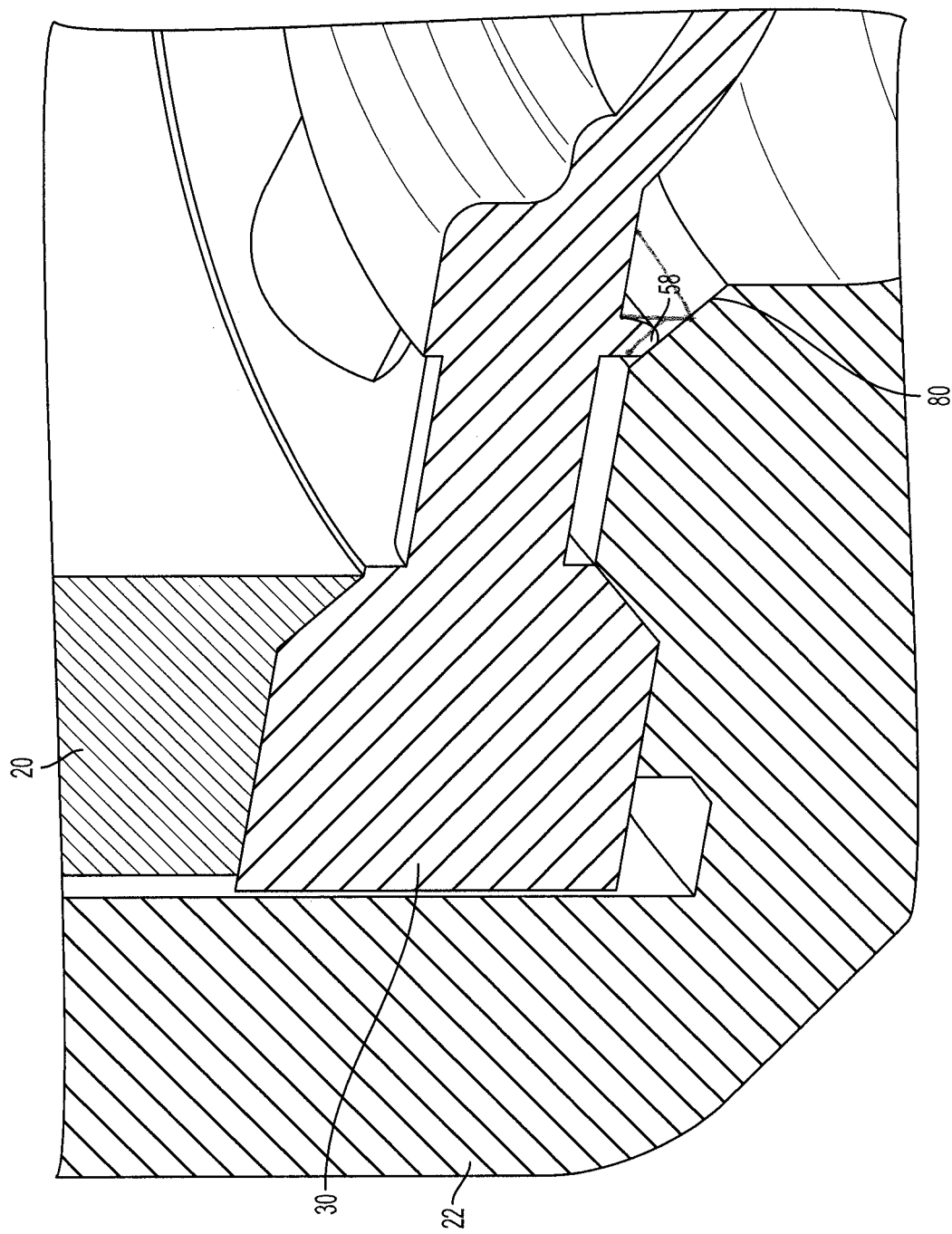
FIG. 11 illustrates an enlarged, partial isometric view of another embodiment of a bi-directional, pressure-actuated valve assembly.

In yet another embodiment, the second housing section 22 of valve assembly 10 may include a seating chamfer surface 80 upon which annular projection 58 rests, as shown in FIG. 11. In this embodiment, seating surface 28 extends inwardly to join seating chamfer surface 80. Seating chamfer surface 80 extends at an inwardly-facing angle toward the longitudinal central axis of lumen 26. Annular projection 58 is compressed against seating chamfer surface 80 to prevent fluid flow during infusion procedures. In one advantage of this embodiment, the sealing surface created by the compressive contact between secondary chamfer surface 80 and annular projection 58 is longer in length than other embodiments and therefore may provide enhanced protection against leakage during both resting state of the valve and during infusion procedures. The angle of seating surface 80 as well as the height and profile of annular projection 58 may be adjusted to customize the threshold pressure at which the second fluid flow path opens to allow fluid to flow. In an additional advantage, the movement of the annular projection 58 along seating chamfer surface 80 as pressure is applied to the diaphragm 30 may have a "wiping" effect to keep surface 80 free from debris buildup.

The location and retention portion of the bi-directional, pressure-actuated valve assembly 10 described herein may vary based on the medical device it is positioned within. Since the flexible diaphragm 30 is compatible with gravity drip infusion, power injection and high-pressure syringe use, it may be incorporated into a variety of vascular and non-vascular access devices. As an example, diaphragm 30 may be positioned within a subcutaneous implantable port to provide bi-directional fluid flow between the port reservoir and catheter shaft. In one embodiment, flexible diaphragm 30 may be compressed between an outlet stem and port reservoir body, or otherwise assembled as disclosed in U.S. Pat. No. 9,205,242, entitled "Port Septum with Integral Valve", which is incorporated herein by reference. For multi-lumen catheters having extension tubing, such as dialysis, PICC and central venous catheters, diaphragm 30 with valve assembly 10 may be attached to the proximal portion of the extension tubing. Alternatively, valve assembly 10 may be positioned within the extension tubing proximal to a bifurcate hub. Diaphragm 30 may also be positioned within a lumen of a hub, wherein the hub internal contours provide the retention function of the valve assembly 10.

Bi-directional, pressure-actuated valve assembly 10 is preferably manufactured using an injection molding process known in the art. Injection molding provides an improved manufacturing process when compared to currently known processes for forming a slitted flat disk valve. Flat disks are usually punched from silicone sheet material. The sheet material characteristics are difficult to consistently control within the desired specification. Therefore, the sheet stock is typically preprocessed prior to forming disk parts. These steps are labor-intensive and may result in a high scrap rate. After punching the disk to form the s valve is assembled into the final valve assembly device. The assembly process has also been found to be problematic as the valve assembly must be cured under closely controlled conditions to ensure the desired amount of disk compression. Due to the nature of the disk material and variations in performance after assembly, the finished valve assemblies typically undergo a secondary process to ensure that the valve continues to open and close at the predetermined pressure thresholds. Testing of valve performance is required after each of these processing steps.

By injection molding the bi-directional, pressure-actuated valve of the invention disclosed herein, many of the costly and time-consuming steps of a flat disk manufacturing process are eliminated. With direct injection molding, there is little of the material waste associated with a sheet stock punching process. The molding process is fast and repeatable, with little variability in the final bi-directional, pressure-actuated valve characteristics and shape. In-process testing steps done to ensure proper cracking thresholds for both aspiration and infusion of flat disks are eliminated, thereby lowering overall costs and increasing throughput. In summary, the method of manufacturing a valve assembly 10 described above streamlines and shortens the manufacturing process, increases production throughput and more efficiently utilizes production resources.

Some embodiments may be described using the expression "one embodiment" or "an embodiment" along with their derivatives. These terms mean that a feature, structure, or characteristic described in connection with the embodiment is included in at least one embodiment. The appearances of the phrase "in one embodiment" in various places in the specification are not necessarily all referring to the same embodiment.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

The invention claimed is:

1. A method for bi-directionally controlling fluid flow through a medical device, comprising:
   inserting a medical device into a patient, wherein the medical device comprises a housing comprising:
   a first housing section and a second housing section;
   a diaphragm having a retention portion positioned between the first housing section and the second housing section, a first flow control portion, and a second flow control portion;
   flowing a fluid in a first direction through the housing, wherein the first fluid flow control portion opens to permit fluid to flow through the diaphragm, and the second fluid flow control portion is compressed against the second housing section to remain closed and prevent fluid to flow between the second fluid flow control portion of the diaphragm and the second housing section;
   flowing a fluid in a second direction through the housing, wherein the first fluid flow control portion remains closed, and the second fluid flow control portion is displaced away from the second portion of the housing to permit fluid to flow between the second fluid flow control portion and the second housing portion; and
   wherein the first direction of fluid flow includes the step of injecting fluid through the diaphragm and the second direction of fluid flow includes the step of aspirating fluid through the diaphragm.

2. The method of claim 1, wherein the medical device is a PICC and the step of injecting fluid includes injecting fluid at a rate up to 5 mls/sec.

3. The method of claim 1, wherein the flow of fluid in a first direction is at a lower rate than the flow of fluid in the second direction.

4. The method of claim 1, wherein the second housing section further comprises a seating surface to seat the second flow control portion against the second housing section to prevent fluid to flow between the second housing section and the second fluid flow control portion when flowing the fluid in the first direction through the housing.

5. A method for bi-directionally controlling fluid flow through a medical device, comprising:
   inserting a medical device into a patient, wherein the medical device comprises a housing comprising:
   a first housing section and a second housing section;

a diaphragm having a retention portion positioned between the first housing section and the second housing section, a first flow control portion, and a second flow control portion;

flowing a fluid in a first direction through the housing, wherein the first fluid flow control portion opens to permit fluid to flow through the diaphragm, and the second fluid flow control portion is compressed against the second housing section to remain closed and prevent fluid flow between the second fluid flow control portion of the diaphragm and the second housing section;

flowing a fluid in a second direction through the housing, wherein the first fluid flow control portion remains closed, and the second fluid flow control portion is displaced away from the second portion of the housing to permit fluid to flow between the second fluid flow control portion and the second housing portion; and wherein the first fluid flow control portion further comprises a dome and at least one slit along the dome.

6. The method of claim 5, wherein the first direction of fluid flow includes the step of injecting fluid through the diaphragm.

7. The method of claim 5, wherein the flow of fluid in a first direction is at a lower rate than the flow of fluid in the second direction.

8. The method of claim 5, wherein the second direction of fluid flow includes the step of aspirating fluid through the diaphragm.

9. The method of claim 5, wherein the diaphragm is comprised of silicone.

10. The method of claim 5, wherein the second housing section further comprises a seating surface.

11. The method of claim 10, wherein the seating surface is configured to seat the second flow control portion against the second housing section to prevent fluid to flow between the second housing section and the second fluid flow control portion when flowing the fluid in the first direction through the housing.

12. The method of claim 5, wherein the medical device is a peripherally inserted central catheter.

13. The method of claim 12, wherein the step of flowing a fluid in a first direction further comprising the step of injecting fluid includes injecting fluid at a rate up to 5 mls/sec.

14. The method of claim 5, wherein the second fluid flow control portion further comprises at least two spokes forming at least one inter-spoke fluid communication channel through which fluid flows in the second direction.

15. The method of claim 14, further comprising the step of:
inserting a second medical device into the housing through the slit.

16. The method of claim 14, further comprising the step of:
flushing the housing after the step of flowing a fluid in a second direction through the housing.

17. A method for bi-directionally controlling fluid flow through a medical device, comprising:
inserting a medical device into a patient, wherein the medical device comprises a housing comprising:
a first housing section and a second housing section;
a diaphragm having a retention portion positioned between the first housing section and the second housing section, a first flow control portion, and a second flow control portion;

flowing a fluid in a first direction through the housing, wherein the first fluid flow control portion opens to permit fluid to flow through the diaphragm, and the second fluid flow control portion is compressed against the second housing section to remain closed and prevent fluid to flow between the second fluid flow control portion of the diaphragm and the second housing section;

flowing a fluid in a second direction through the housing, wherein the first fluid flow control portion remains closed, and the second fluid flow control portion is displaced away from the second portion of the housing to permit fluid to flow between the second fluid flow control portion and the second housing portion; and wherein the first fluid flow control portion extends away from the second fluid flow control portion in a distal direction.

18. The method of claim 17, wherein the flow of fluid in a first direction is at a lower rate than the flow of fluid in the second direction.

19. The method of claim 17, wherein the medical device is a peripherally inserted central catheter.

20. The method of claim 19, wherein the step of flowing a fluid in a first direction further comprising the step of injecting fluid includes injecting fluid at a rate up to 5 mls/sec.

* * * * *